United States Patent [19]

Orimo et al.

[11] 4,338,279

[45] Jul. 6, 1982

[54] AUTOMATIC ANALYZING APPARATUS

[75] Inventors: Ryoichi Orimo, Ohme; Masahiko Sakurada, Machida; Taiichi Banno, Hachioji; Sugio Manabe, Kodaira, all of Japan; Kevin Galle, New York, N.Y.

[73] Assignee: Olympus Optical Company Limited, Tokyo, Japan

[21] Appl. No.: 139,470

[22] Filed: Apr. 11, 1980

[30] Foreign Application Priority Data

Apr. 14, 1979 [JP] Japan .................................. 54-44911

[51] Int. Cl.³ ...................... G01N 35/04; G01N 35/06
[52] U.S. Cl. ........................................ 422/64; 422/65; 422/67; 364/497
[58] Field of Search ................... 422/63, 64, 65, 67; 364/497, 498; 356/222

[56] References Cited

U.S. PATENT DOCUMENTS 3,969,079 7/1976 Catarious et al. ................ 422/64 X
4,061,469 12/1977 Du Bose ........................... 422/67 X
4,234,538 11/1980 Ginsberg et al. ................. 422/67 X Primary Examiner—Ronald Serwin
Attorney, Agent, or Firm—Stevens, Davis, Miller and Mosher

[57] ABSTRACT

An automatic chemical analyzing apparatus comprising means for feeding successive reaction vessels along a circular reaction line, a sample delivery pump for delivering a given amount of sample liquids to be tested into the reaction vessels, a reagent delivery pump for delivering a given amount of reagent (corresponding to a particular test item to be measured) selected from a plurality of reagents, a first photometering means provided along the circular reaction line for monitoring the reaction condition of a test liquid in the reaction vessel on the reaction line, a second photometering means arranged in a precise photometering section positioned underneath the reaction line, means for transporting the reaction vessel from the reaction line into the precise photometering section after the test liquid in the relevant vessel has been monitored to reach a given reaction condition.

50 Claims, 55 Drawing Figures

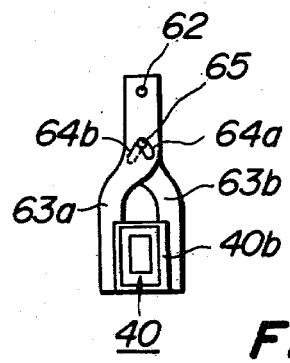
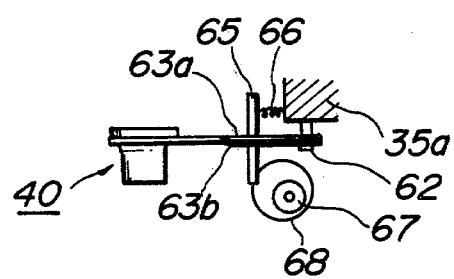
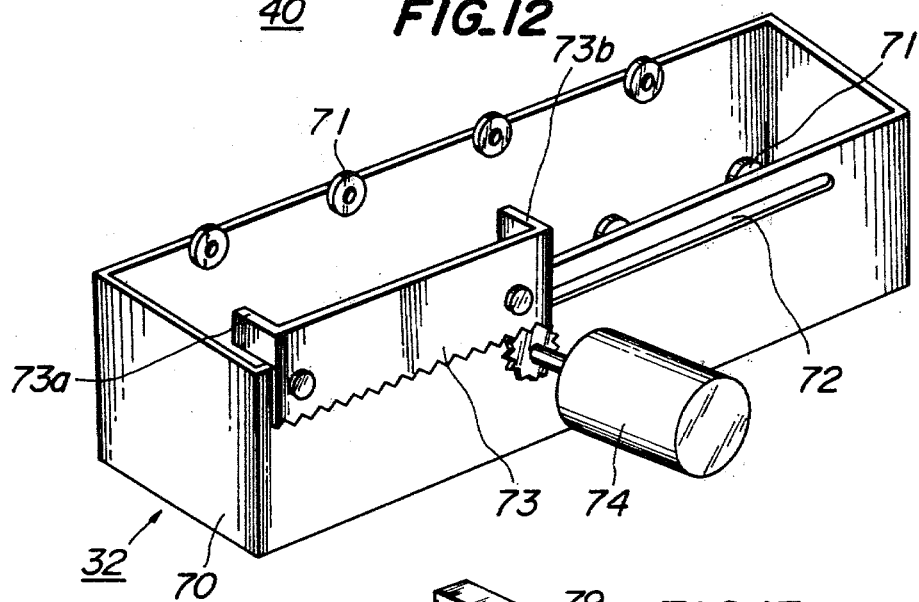
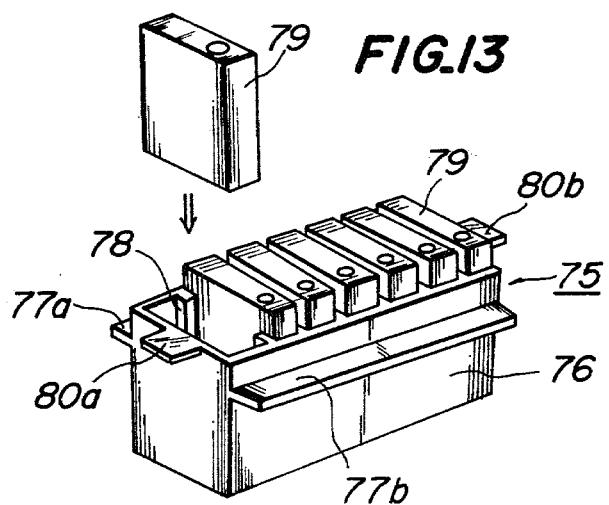

FIG.23
FIG.24
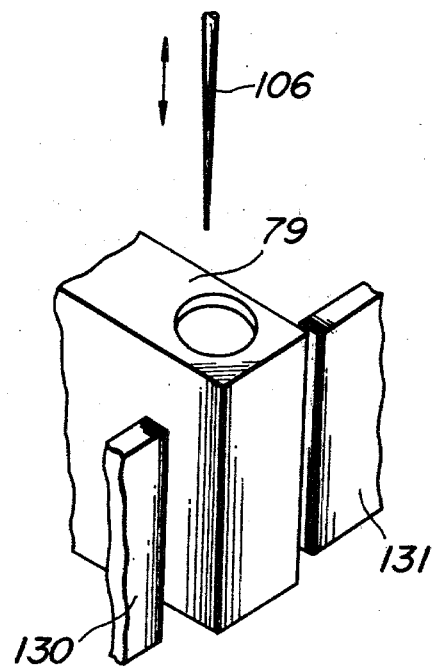
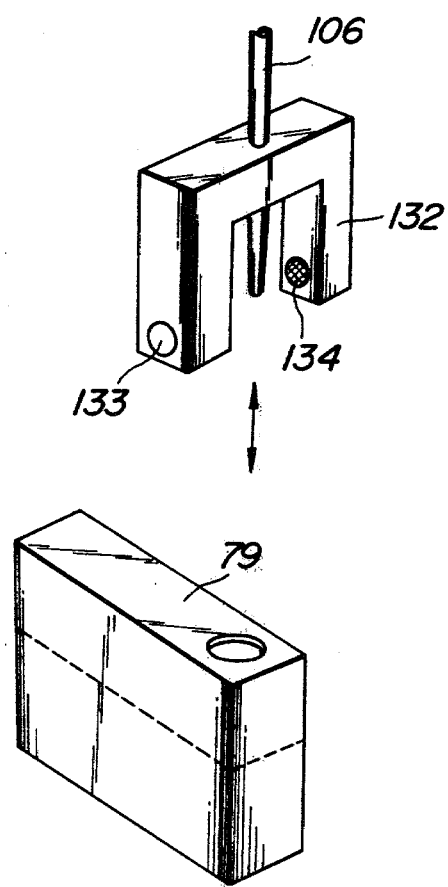

FIG. 36

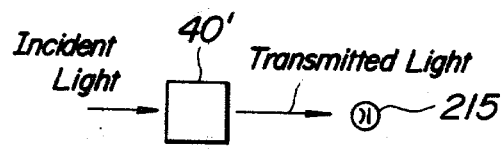
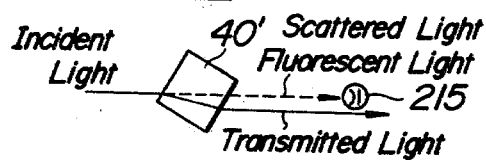
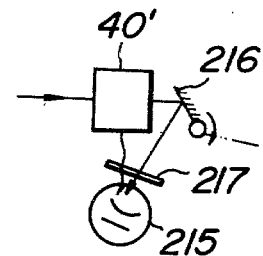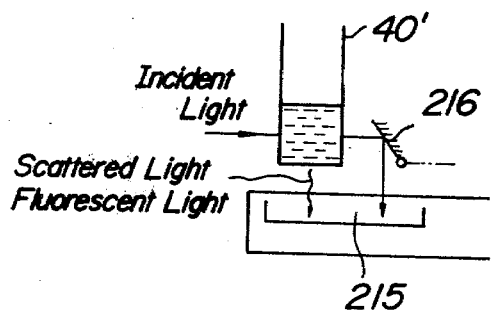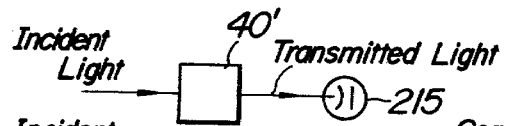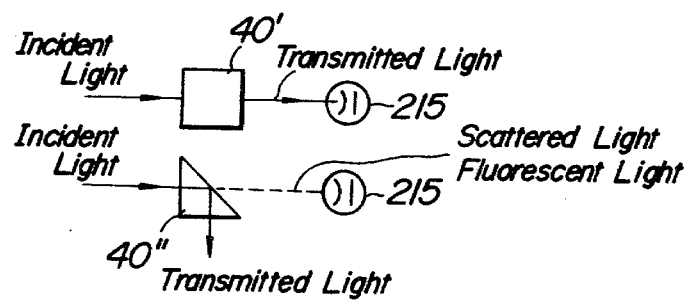

AUTOMATIC ANALYZING APPARATUS

BACKGROUND OF THE INVENTION

This invention relates to an automatic analyzing apparatus for automatically effecting chemical analyses for various sample fluids such as (but not limited to): cerebrospinal fluid, blood, urine, and the like.

Automatic chemistry analyzers can be roughly divided into two broad categories: continuous flow or discrete systems. Presently the majority of analyzer models employ the discrete approach to automation.

In a discrete system, each test is carried through the analytical process in its own dedicated (discrete) container or compartment. Current discrete analyzers can be further classified into two major sub-categories; sequential and centrifugal analyzers.

In sequential testers, all tests are performed sequentially, one after another, so that at any given point in time all tests in process are in a somewhat different state of progress. In general, sample and reagent are metered into a vessel which is fed along a given path and the test liquids in each of the vessels are treated to each aspect of the analysis (reagent addition, mixing, quantitating, etc.) in sequence.

Centrifugal analyzers are also discrete but test liquids are processed in parallel to one another. All samples in process are in the same stage of analysis at the same time. In operation, samples and reagent are pre-measured and pre-loaded into appropriate compartments arranged about the circumference of a rotor disc, whereupon it is placed on a centrifuge and rotated at a high speed past a photometer device. Centrifugal force mixes all samples with reagent at the same time and hence each of the test liquids is in the same stage of analysis at any given point in time.

The majority of analyzers, regardless of the above mentioned categories, are capable of performing more than one type of test item. There are three broad categories of methods for providing for multi-test capability.

What shall hereinafter be referred to as Random Access Testers currently require individual test packs which are pre-packaged with the appropriate reagents required to perform one test of a given test type. These test packs are loaded into the instrument system according to the analyst's needs, charged with a sample liquid, and processed in a discrete manner. Random access testers offer great convenience and flexibility but currently available embodiments have low productivities when compared with other means of providing multi-test item capability. In addition, the requirement for pr-packaged test packs makes operating costs much higher than the alternate methods.

Another means of performing a plurality of tests on each of a plurality of samples is sequentially by test-item batch. All samples are analyzed sequentially or centrifugally for a given test item. When all samples have been analyzed for a given test item, the system is changed over, or somehow modified, to perform a different test item and all appropriate samples are re-treated. When all samples have been processed for the required test items, the results of each samples' test items must be collated to allow including all of a given samples analytical results on a single report form for return to a physician, etc. Such systems are usually referred to as 'single channel' systems. Single channel systems are usually considered most appropriate for treating a batch or plurality of samples, as the effort required to change-over from one test item to another is generally neither convenient nor cost-effective to treat one sample for a plurality of test items. Additionally, at any given moment in time, only one test item is available for immediate use.

Simultaneous analyzers have a plurality of analytical channels which enable a plurality of test items to be performed simulultaneously on each sample. Such systems are commonly referred to as 'multi channel' analyzers. Multi-channel analyzers do make more than one test item available at any given point in time, do eliminate the data collating task required of single channel analyzers and in general, do have higher productivities than single-channel analyzers by virtue of the fact that they are constructed as a plurality of single-channel analyzers combined into one device. This last feature is a drawback in that it makes the analyzer system complicated in construction, large in size, and generally, much higher in cost than single-channel discrete, continuous flow or centrifugal analyzers.

In the known analytical systems of the noncentrifugal type, photometric quantitation is carried out after some time period from the initiation of the test reaction, i.e. when the test liquid has traveled along the processing line by some given fixed distance. Therefore, the reaction time is fixed as a function of the length or circumference of the processing line, which may or may not be optimal with respect to a given test item and/or sample.

Additionally, sequential testers have only one photometer position per channel, severely limiting the amount of photometric data which can be made available. No photometric data can be made available until a test liquid reaches the photometer station, typically, 8–10 (often 30) minutes from the time of mixing of sample with reagent. Once a test liquid reaches a photometer station, the amount of time which is devoted to photometric measurement essentially limits the speed of analysis of a given sequential tester, i.e. if 60 seconds is devoted to photometric quantitation, then the processing rate is limited to 60 tests per hour. This feature forces a trade-off between processing rate and photometric quantitation time especially for 'kinetic' tests (ex. enzyme rate tests) which require photometric measurement over long periods of time in order to provide for best accuracy and precision of analysis.

SUMMARY OF THE INVENTION

The present invention has as its object to provide for an automatic analyzing apparatus which is so constructed that the above drawbacks can be avoided while insuring consistently reliable results.

According to the invention, an apparatus for effecting automatic analysis comprises means for successively feeding reaction vessels, each containing a respective test liquid to be analyzed, along a given reaction line;

Means for delivering (a) given amount(s) of (a) given reagent(s), corresponding to a test item to be measured, into a reaction vessel on the reaction line to form a test liquid;

First photometering means arranged in a reaction-condition-monitoring-section provided along the reaction line for monitoring the reaction condition of test liquid in the vessel;

Means for transporting at least the test liquid into a precise photometering section positioned apart from the reaction line, after the first photometering means have detected that the test liquid has reached a given reaction condition;

Second photometering means arranged as part of a precise photometering section for effecting quantitative analysis of a given test item for a given sample liquid; and Means for discharging the test liquid out of said precise photometering section, after the quantitative analysis for a given test item has been performed.

BRIEF DESCRIPTION OF THE DRAWINGS

FIGS. 11a and 11b are a plan view and a side view, respectively, illustrating an embodiment of a cuvette holding and releasing mechanism;

FIG. 12 is a perspective view showing one embodiment of a cassette holder shown in FIG. 4;

FIG. 13 is a perspective view depicting an embodiment of a reagent cassette to be removably installed in the cassette holder of FIG. 12;

FIG. 23 is a perspective view illustrating an embodiment of a liquid level detector for reagent in a reagent bottle;

FIG. 24 is a perspective view showing another embodiment of the reagent level detector;

FIG. 36 is a plan view showing a format of a patient card for use in the patient-data system shown in FIGS. 34 and 35;

FIGS. 44a and 44b are schematic views illustrating an embodiment of the photometric section in which the transmitted, scattered and fluorescent light is received by a single light receiving element;

FIG. 45 shows another embodiment of the photometric section;

FIG. 46 illustrates still another embodiment of the photometric section; and

FIGS. 47a and 47b are schematic views illustrating another embodiment of the photometric section in which the scattered, transmitted and fluorescent light can be received by a single element by using cuvettes having different configurations.

DESCRIPTION OF THE PREFERRED EMBODIMENTS

Figure 1:
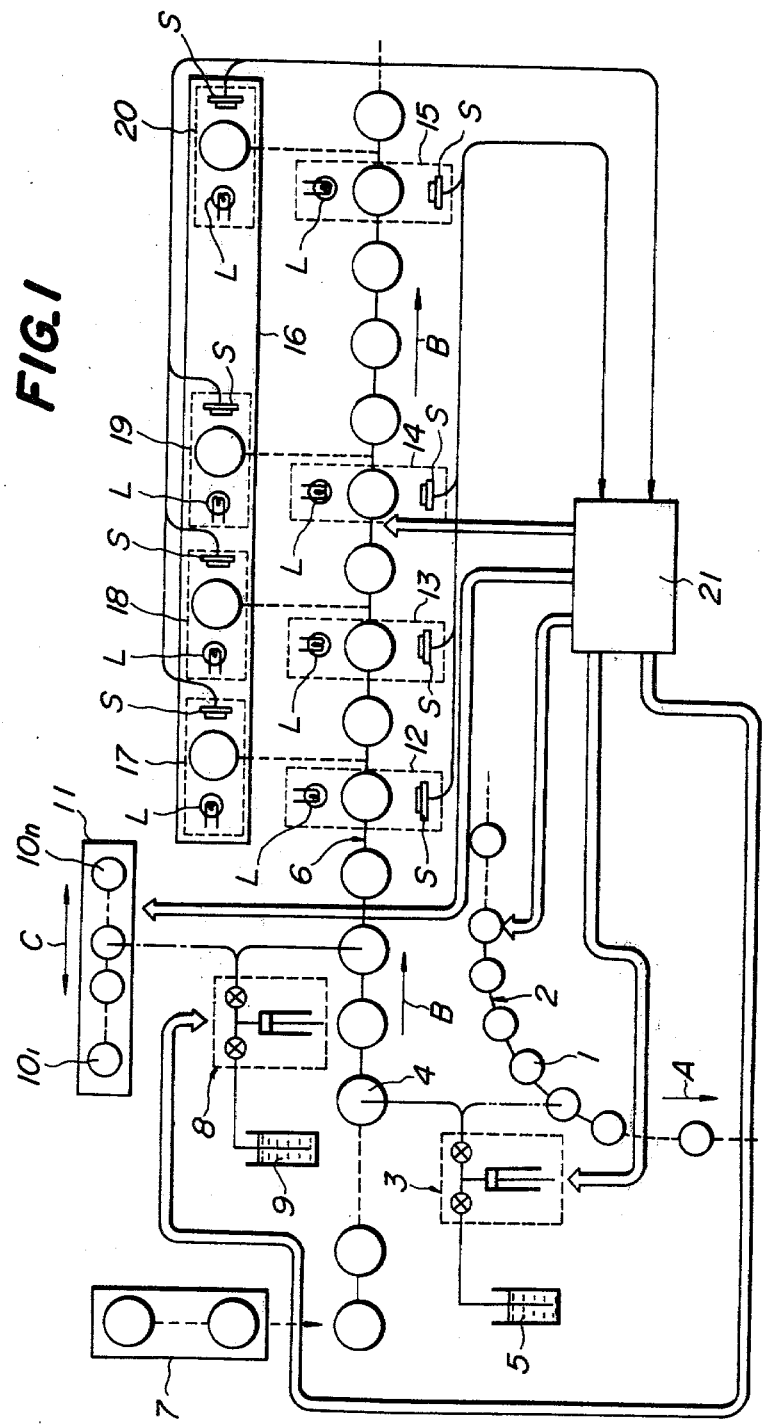
FIG. 1 is a schematic view illustrating a principal construction of an automatic analyzing apparatus according to the invention.

FIG. 1 is a schematic view illustrating a constructional principle of the automatic analyzing apparatus according to the invention. This apparatus can be classified as a discrete system adopting a batch process and belongs to a sequential multi-test system in which analyses for a plurality of test items can be effected continuously in succession. Sample vessels (1) are supported on a sample feed mechanism (2) and are intermittently fed in a direction shown by an arrow (a). A given amount of sample liquid, contained in the successive sample vessels (1), are aspirated by a sample delivery mechanism (3) at a given position in accordance with test items to be analyzed, and the given amount of sample liquid is supplied into cuvettes (4) together with a diluent as required (5). The cuvettes (4) are supported by a cuvette-feed mechanism (6) and are intermittently fed along a reaction line (b) in a direction shown by an arrow (b) at a pre-determined period, such as six seconds per step. New cuvettes (4) are successively supplied to the feed mechanism (6) from a cuvette-delivery mechanism (7). The cuvette (4) having the sample liquid delivered therein is advanced by several steps and arrives at a given position, at which point a reagent, dependent on the test item to be measured, is delivered into the cuvette (4) together with a diluent (9) by means of a reagent-delivery mechanism (8). Reagents to be used for measurement are contained in reagent bottles ($10_1$–$10_n$) which are supported on a reagent-feed mechanism (11) moveable in a reciprocal manner as shown by a double headed-arrow (c).

A given reagent can be drawn by the delivery mechanism (8) from the bottle which is positioned at the given delivering position. The sample liquid and reagent can be sufficiently mixed by jetting the reagent into the cuvette (4) together with the diluent at a suitable flow rate. The cuvette (4) having had reagent and sample delivered thereto travels along the reaction line (b). The test liquid in the cuvette is measured by four photometers (12 to 15) comprising a light source (l) and a light-receiving element (s) provided at positions corresponding to 12, 24, 36 and 60 seconds after the reagent delivering position, i.e. the cuvette (4) having reagent delivered therein has moved by 2, 4, 6, and 10 steps, respectively. In this manner the reaction state of the test liquid in the cuvette (4) can be monitored as it progresses along the reaction line.

Figure 2:
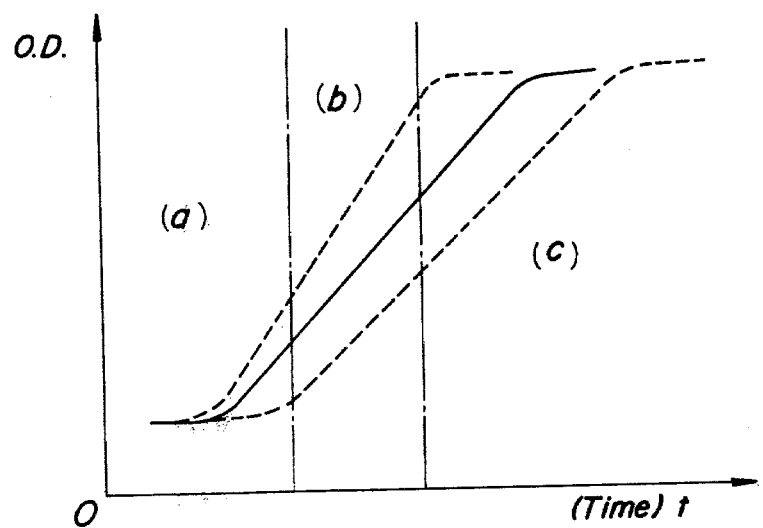
FIG. 2 is a graph showing typical reaction kinetics of a test liquid.

Particularly in the measurement of enzymatic reactions, it is very important to monitor the reaction over some extended period of time. That is to say, in the measurement of enzymatic reactions, it is impossible to obtain an accurate result unless a measurement is effective during the linear portion of an absorbance level-to-time characteristic curve. In FIG. 2, a typical reaction curve is shown with absorption (O.D.) plotted on the ordinate, and time (t) measured from the addition of reagent, plotted on the abscissa. In FIG. 2, the left-hand zone (a) represents the lag phase of reaction due to heating time of test liquid, mixing, etc. and zone (b) denotes the linear phase in which the reaction rate measurement, i.e. kinetic reaction measurement, can be effected positively and accurately. Further, zone (c) represents an end point phase in which the reagent substrate or other given components in the test liquid have been exhausted. Measurement in the end point zone (c) results in erroneously low values when performing kinetic assays. The period of the linear phase (b) may be suitable changed by adjusting the substrate concentration, etc. and total volume of test liquid. This adjustment is effected in such a manner that the end of the lag phase (a) can be detected by the photometers (12 to 15) (see FIG. 1) for almost all test liquids, even if the test liquids have fast or slow reaction rates. Preferably, the substrate concentration conditions, and total volume of test liquid are so adjusted that a variation in absorption can be observed after twelve seconds (corresponding to the position of photometer 12) from the mixing of reagent and sample for the test liquid having the slowest reaction rate, and the linear phase (b) will last for one or two minutes or more for the normal test liquids. By such a measure, the lag phase of successively fed test liquids can be monitored in a substantially completed state by the photometers (12 to 15). It should be noted that since the photometers (12 to 15) are used to detect only the end of the lag phase (a), they may have lower accuracy. That is to say, relatively unsophisticated photometers can be used.

As shown in FIG. 2, a precise photometer sec. (16) is provided near photometers (12 to 15) for monitoring the lag phase, but apart from the reaction line (b). The precise photometer section (16) comprises accurate photometers (17 to 20) each consisting of a light source (l) and a light-receiving element (s). When the end of the lag phase of a test liquid is detected by one of the photometers (12 to 15), the test liquid is transported together with the cuvette (4) from the reaction line (b) to one of the photometers (17 to 20) which is not occupied by another test liquid. Then the test liquid is measured for twelve seconds and is thereafter discharged together with the cuvette (4). In this manner, measurement at a precise photometer section (16) is effected during the linear phase of the reacting kinetics for a sufficient length of time, and thus reliable data of high accuracy can be obtained. The photometering step at section 16 is twelve seconds, which is twice as long as the feed step period (six seconds) of the cuvette along the reaction line (b). However, this causes no problem, as the four photometers for precise measurement are provided apart from the reaction line. Therefore, photometric measurement can be effectively carried out without changing the cuvette feed step on the reaction line (B) and thus, the handling efficiency can be improved. If the linear phase is detected by any one of photometers (12 to 15), but a photometer in the precise measurement section (16) corresponding to the related photometer has been occupied by another test liquid, the cuvette feed mechanism (6) moves the related cuvette by several steps forward or backward during one stepping period so as to transport the cuvette into a photometer in section 16 which is not occupied by another test liquid. After which mechanism (6) returns to a position preceding the original position by one step and the cuvettes are once again transported successively, step by step.

The operation of the above described sample feed mechanism (2), sample delivering mechanism (3), cuvette feed mechanism (6), reagent delivering mechanism (8), and reagent feed mechanism (11), the monitoring action for lag phase and the precise measurement in the linear phase can be controlled by a control device (21) comprising an electronic computer.

According to one aspect of the invention, any lag phase is monitored on the reaction line, and the actual photometric measurement is carried out at a position apart from the reaction line after the beginning linear phase has been detected. By such a measure it is possible to realize an automatic analyzing apparatus which can obtain analyzed data of high accuracy and high reliability as well as high productivity, because a sufficiently long measuring time can be attained at a position apart from the reaction line without disturbing the sequencing of the reaction line.

EMBODIMENTS OF THE APPARATUS ACCORDING TO THE INVENTION

Figure 3:
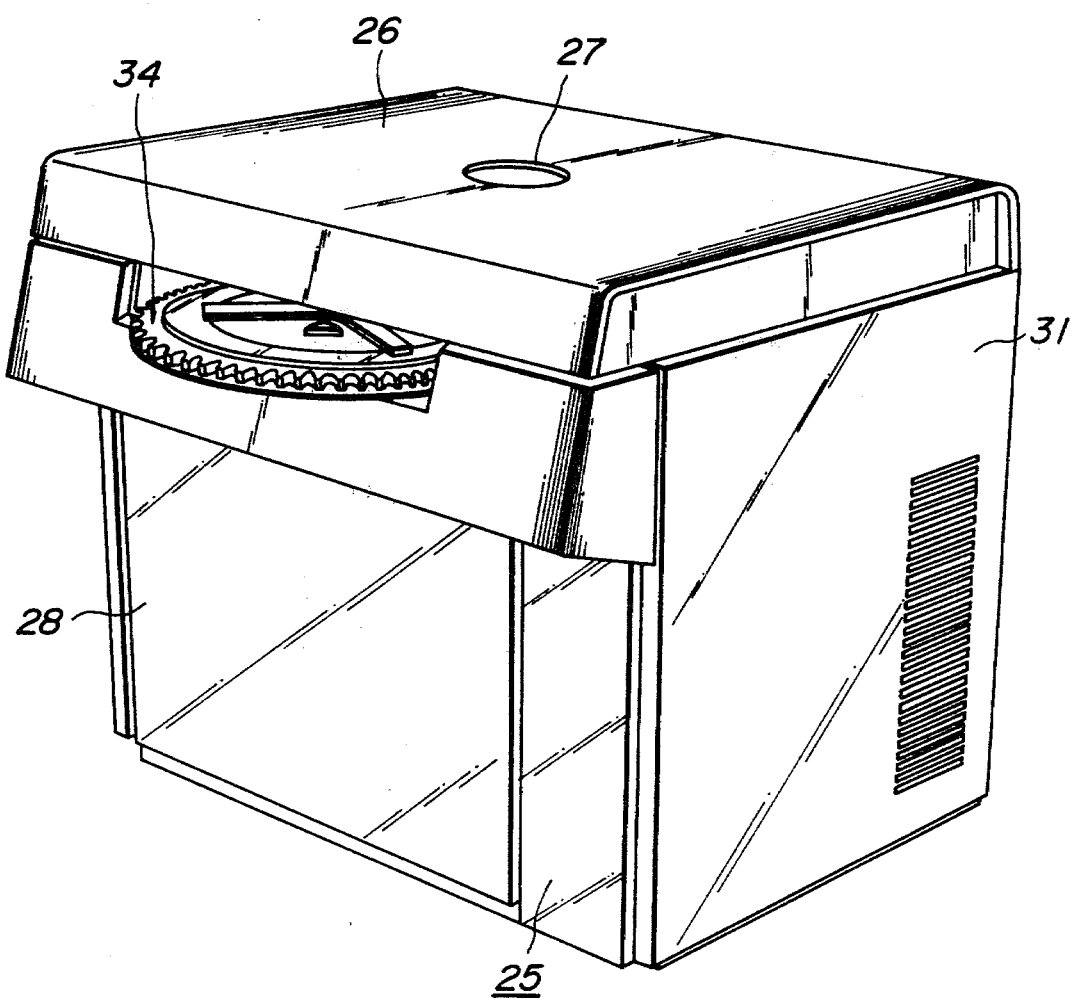
FIGS. 3 and 4 are perspective views illustrating an embodiment of the automatic analyzing apparatus of the invention.
Figure 4:
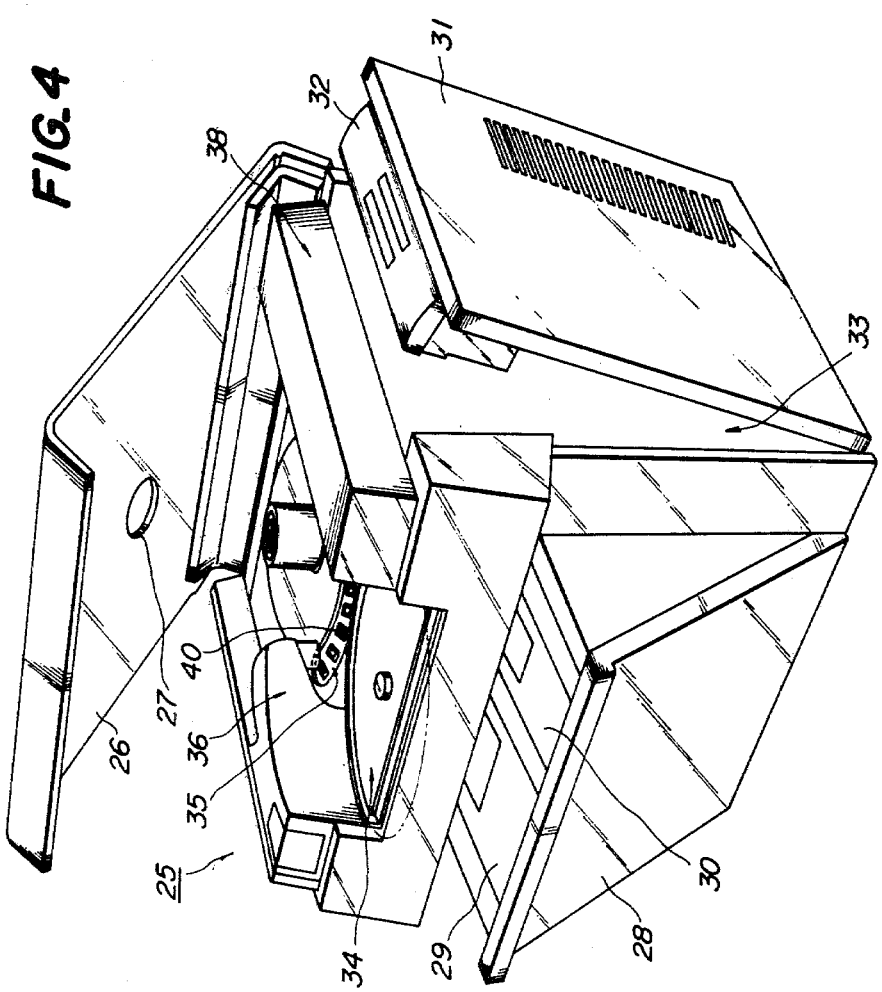

FIGS. 3 and 4 are perspective views illustrating an outer appearance of the automatic analyzing apparatus according to the invention. A main body (25) includes a cover (26) hinged at the rear to provide access to internal components. In the cover (26) are openings (27a and 27b) for dissipating heat produced by light sources of the photoelectric colorimeters. A front plate (28) is secured to the main body (25) in such a manner that the front plate can be opened to provide access. A cuvette container (29) for storing waste cuvettes and a waste liquid container (30) for storing waste liquid are detachably secured to the front plate (28). A right-hand side plate (31) is hinged to the main body (25) at the bottom side, and a cassette holder (32) for supporting a detachable reagent cassette for holding various reagent bottles necessary for given analyses is provided on the side plate (31). A portion for fitting the cassette holder (32) defined by the right-hand side plate (31) forms a refrigerator (33).

Figure 5:
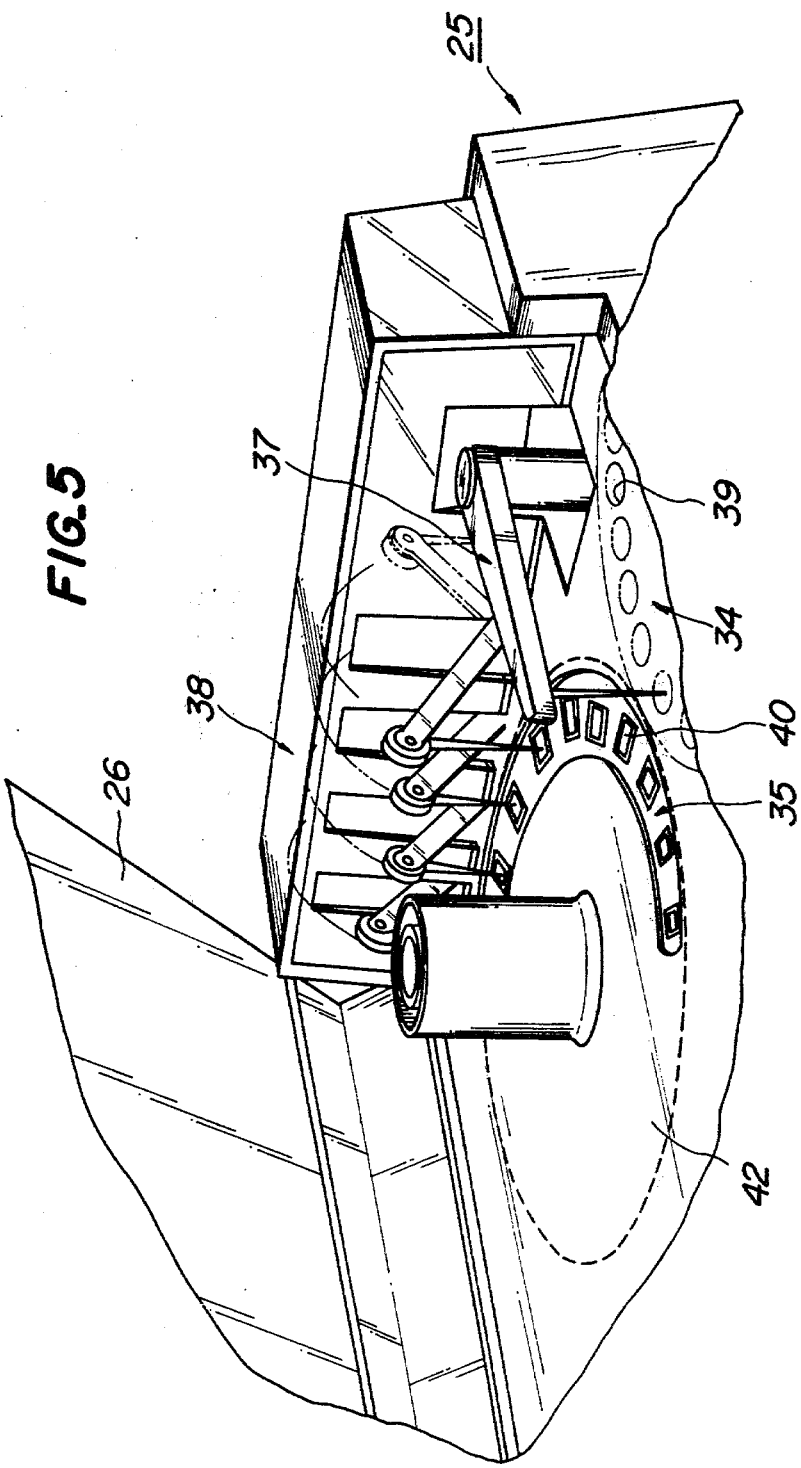
FIG. 5 is a perspective view showing a sample and reagent delivery section of the apparatus shown in FIGS. 3 and 4.

A sample-liquid feed mechanism (34), a cuvette feed mechanism (35), and a cuvette supply mechanism (36) are provided on the main body (25) at its front portion, back portion and left hand portion, respectively. As shown in FIG. 5 at the right hand portion of the main body (25) are provided a sample delivery mechanism (37), and a reagent delivery mechanism (38). In this embodiment, the reagent delivery mechanism (38) comprises four reagent delivering pumps connected to different diluents and/or buffer solutions.

The sample liquid feed mechanism (34) and cuvette feed mechanism (35) comprise disc-shaped rotating members which can rotate intermittently in a horizontal plane and hold detachable sample vessels (39), and cuvettes (40), respectively along their peripheries.

Figure 6:
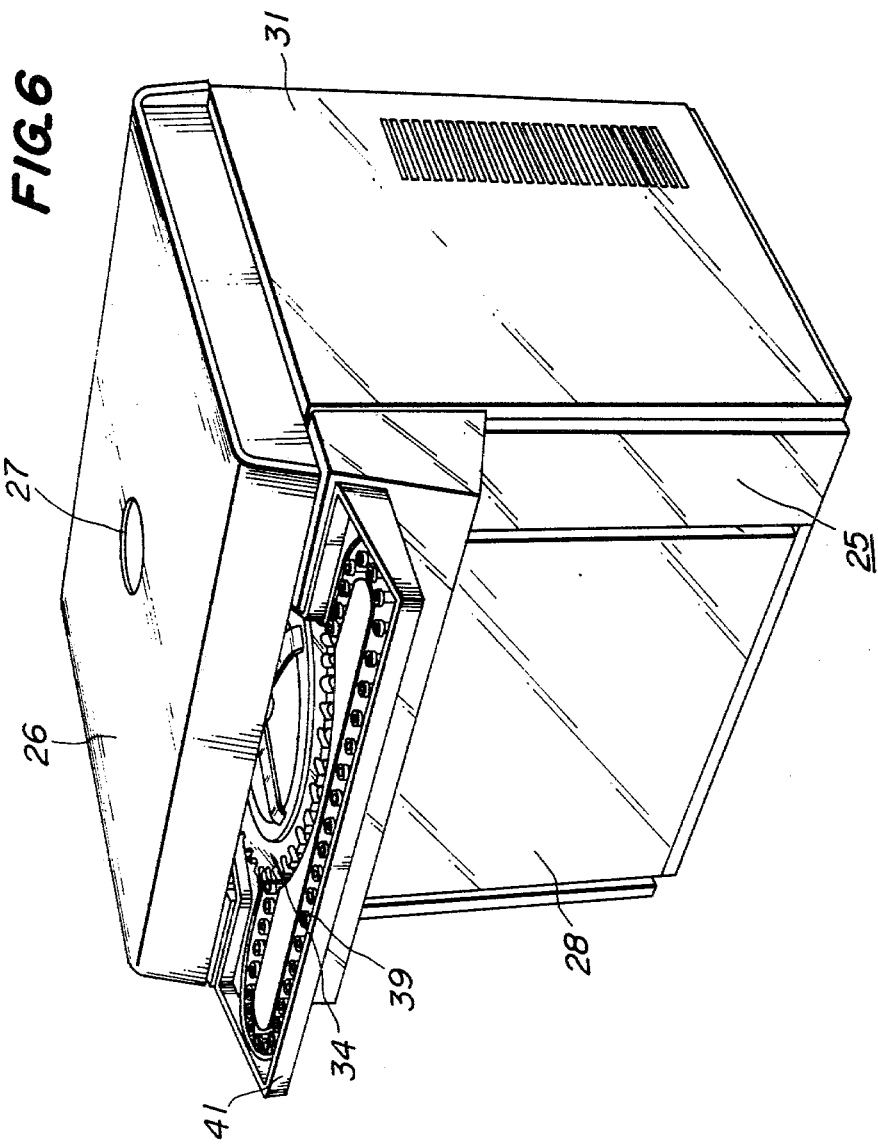
FIG. 6 is a perspective view showing the apparatus having a sample-carrier adaptor secured thereto.

Further in the present embodiment, as shown in FIG. 6, a sample-carrier adaptor (41) may be secured to the front side of the main body so as to be easily removable and replaceable, so as to increase the capacity of the sampler module as necessary. To this end, the sample-carrier adaptor (41) comprises a sample chain which extends over a rotating member of the sample feed mechanism (34), and engages with what are otherwise sample vessel holding portions of the rotating member. A number of sample carriers (39) are detachably secured to the sample chain. The rotating member serves as a sprocket to rotate the sample chain, and a great number of sample carriers can be optionally driven by means of a common driving source.

As illustrated in FIG. 5, a cover (42) is provided for covering the cuvette travelling line, i.e. the reaction line of the cuvette feed mechanism (35) from the reagent delivery section to the cuvette supply section. Underneath the cover (42) is arranged the lag phase monitoring section which comprises a plurality of lag phase monitoring photometers arranged along the reaction line. Underneath the lag phase monitoring section, is provided apart from the lag phase monitoring section, a precise photometry section comprising a plurality of photometers, each corresponding to respective lag phase monitoring photometers. In this embodiment, the feeding step time of the cuvettes on the reaction line is six seconds, and that on the precise measuring section is twelve seconds.

Next the lag phase monitoring section and the precise photometric section will be explained with reference to FIGS. 7 and 8, which illustrate schematically, plan and cross sectional views respectively thereof. The lag phase monitoring section (43) is arranged along that portion of the reaction line of the cuvette feed mechanism (35) which is covered by cover 42, and comprises four lag phase monitoring photometers provided at positions 44 to 47, at which a cuvette (40) situated at the last reagent delivery pump, will arrive after 12, 24, 36, and 60 seconds, respectively. The lag phase monitoring is effected through the cuvette. The precise photometry section (48) is arranged underneath the lag phase monitoring section (43), and comprises cuvette holding members, arranged at positions corresponding to the lag phase monitoring positions (44 to 47), for supporting cuvettes (40) lowered from those positions. The precise photometric measurement is also effected through the cuvette, but for twelve seconds. After measurement, the cuvette (40) is dropped from the holding member. and the cuvette (40) and waste liquid are separated by a separating means (which will be explained later) and are separately collected by a waste cuvette container (29), and a waste liquid container (30) (see FIG. 4).

In this embodiment, the photometers of the lag phase monitoring section and precise measuring section commonly utilize a single light source for emitting a white light. At the center of rotation of the cuvette feed mechanism, is vertically arranged a cylinder (50), which communicates with opening 27 formed in cover 26 (shown in FIG. 3), a light source (51) and a multifaceted mirror (52) are arranged within the cylinder. Lenses (53) are secured to cylinder 50 at levels corresponding to the lag phase monitoring positions and precise measuring positions. At each lag phase monitoring position are arranged an optical filter (54), and a photo detector (55) on opposite sides of the cuvette travelling path of cuvette feed mechanism 35. Similarly, at each precise photometric position are arranged an optical filter (56) and a photo detector (57) on opposite sides of the cuvette (40). The filter (56) of the precise measuring section, comprises a plurality of filter elements having different transmitting wave lengths and secured to a filter-holding member (58) rotatably arranged around cylinder 50. In this manner, the filter element of a wave length required by a particular test item can be selectively introduced and thus highly accurate data can be obtained by a multiple wave length measurement. Light rays radiated from the lag phase monitoring section (43) are projected to the cuvettes (40) on the reaction line by means of the multifaceted mirror (52), lenses (53), and optical filters (54); light rays passing through the cuvettes are received by photo detectors (55) to monitor the lag phase of the test liquid at monitoring positions 44 to 47. At the precise measurement section (48), light rays from light source 51 are projected to the cuvettes (40) by means of the lens (53) and the filter (56) for transmitting light having the desired wave length(s) (selected in accordance with the test items). Light rays passing through the cuvettes are detected by photo detectors (57) so as to effect measurement during the linear phase, at a respective precise measuring position.

Through the reaction line of the cuvette feed mechanism (35), and the precise measuring section (48), is circulated air heated to a typical temperature of 37° C. so as to constitute a temperature-controlled environment. At the bottom of cylinder 50 is provided a fan (59) which dissipates heat produced by the light source (51) through tube 50, and opening 27, of cover 26 shown in FIG. 3.

Now the operation of the apparatus mentioned above will be briefly explained.

Sample fluids taken from patients are delivered into sample cups (39) which are then set into the sample feed mechanism (34), which rotates intermittently. To the cuvette feed mechanism (35), which rotates intermittently in the direction (D) at the rate of one step per six seconds, are successively supplied cuvettes from cuvette supply mechanism 36. Into the cuvette loaded into the cuvette feed mechanism (35) is delivered sample and diluent at a given position by means of sample delivery mechanism 37.

After the cuvette has been moved by several steps, given reagent and diluent (or buffer solution) are delivered into the cuvette by means of a reagent delivery pump connected to a given diluent and/or buffer solution. During this delivery, the contents in cuvette are mixed with each other to form a 'test liquid'. The test liquid is fed by the cuvette feed mechanism (35) along the reaction line and through a plurality of photometric positions (44 to 47) of lag phase monitoring section 43, and the end of the lag phase is detected through the cuvette (40). When the end of lag phase has been detected, the cuvette falls into an empty precision measuring position of section 48 during the next sycle and is photometrically observed for twelve seconds. After precise measurement, the cuvette (40) and its contents are separately discharged to a waste cuvette container (29) and a waste liquid container (30).

Figure 7:
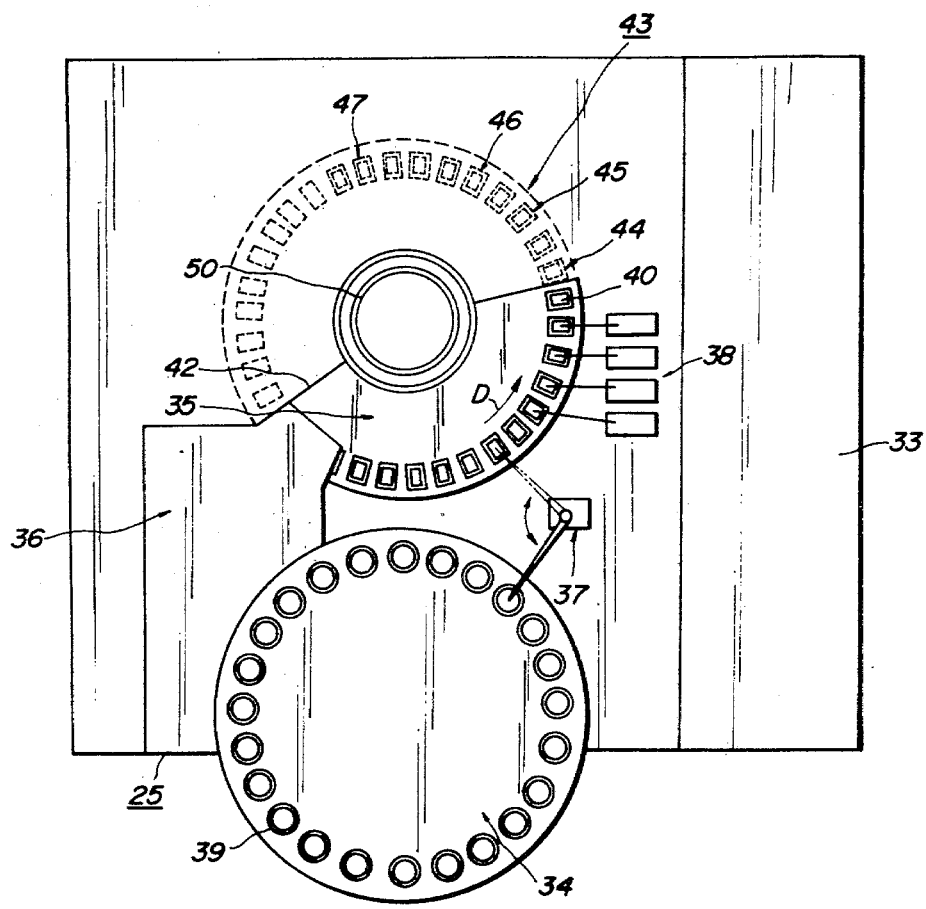
FIG. 7 is a plan view showing schematically the apparatus of FIGS. 3 and 4.
Figure 8:
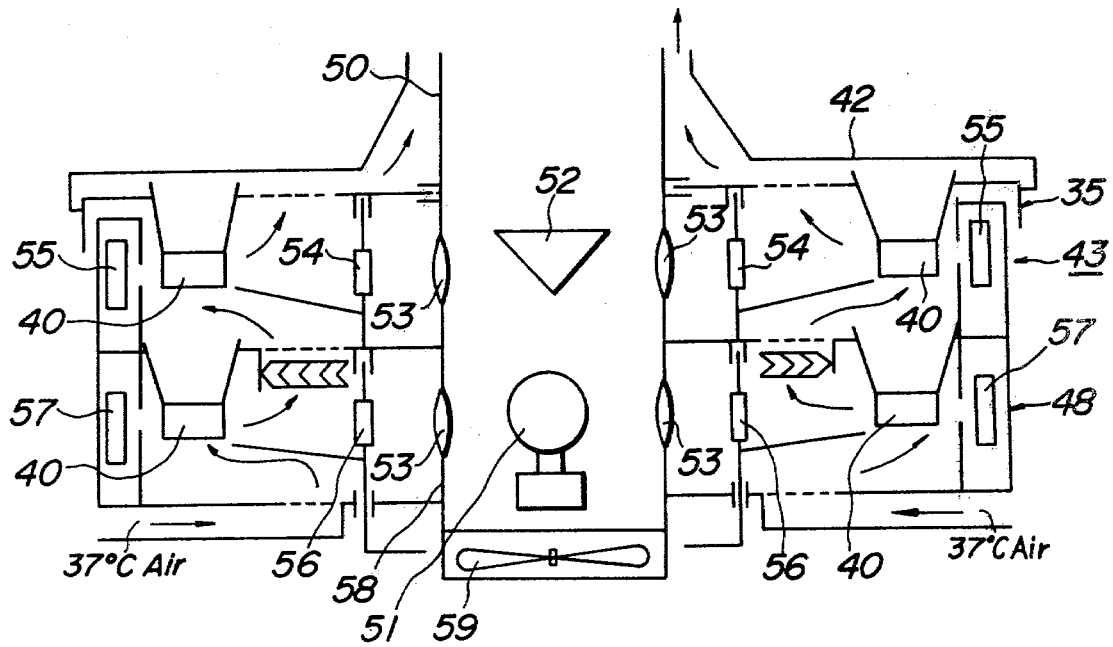
FIG. 8 is a schematic cross section showing in detail a 'lag phase' monitoring section and a precise measuring section.

While FIGS. 6 and 7 show two sets of slits, filter assemblies, and photodetectors, any number of such 'optical channels' may be provided.

It should be noted that since in this embodiment use is made of sequential multi-test mode, it is, of course possible to measure continuously a plurality of test items for each sample as desired by the operator, and supplied to the computer-control device via keyboard, cards or other commonly used computer input devices, etc.

It should be noted that this embodiment offers an operator a number of choices which heretofore would require a sacrifice in productivity and/or convenience to obtain the desired combination of data gathering modes and/or capabilities as follows:

a. Monitoring the change in absorbance of a test liquid over time with capabilities for selectively determining the linear phase of the reaction.

b. Performing such monitoring as in 'a.' above at two or more wavelengths.

c. Gathering data for test liquids at only one or two points in time (herein referred to as end-point assays) at one more wavelengths when such desired test liquids are randomly interspersed on the turntable with test liquids requiring data gathering modes as in 'a.' or 'b.' above.

D. Conversely, test liquids requiring data gathering modes as in 'A.' 'B.' above can be randomly interspersed on the turntable with end point assays as in 'C.' above.

E. It is further possible to effect continuously a single test item for all samples utilizing any or all of data modes 'A.' through 'C.' above or;

F. To treat a plurality of samples to a plurality of test items utilizing any or all of the data acquisition modes as in 'A.' through 'C.' above.

The apparatus of this embodiment further includes the ability for automatic calibration. This can be effected by setting a standard sample to the sample feed mechanism (34) during a stand-by condition. Then, the apparatus automatically operates at every constant time period and the standard sample is delivered into the cuvette (45) on the cuvette feed mechanism (37) and the automatic calibration is effected in a usual manner to compensate for drifts of the apparatus such as variation in brightness of the light source (46), etc.

This automatic calibration ability allows the instrument to be used at any time of day or night with complete confidence that the calibration routine is properly performed regardless of the relative expertise or attention of the operator.

The control of operation of various portions, the inputting operation of patient or sample information, and the calculation of the analyzed results can be effected by a control device (not shown) including one or more computers.

Figure 9:
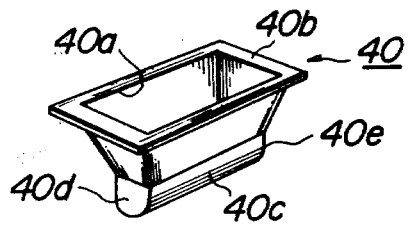
FIG. 9 is a perspective view showing an embodiment of a cuvette for use in the apparatus according to the invention.

FIG. 9 is a perspective view illustrating an embodiment of the cuvette (40). The cuvette (40) of this embodiment comprises a rectangular opening (40a) and a supporting flange (40b) provided at the periphery or opening. The opening is connected to a bottom portion (40c) by a tapered side wall narrowing towards the bottom portion. The bottom portion (40c) is formed as a semi-cylindrical shape and has measuring windows (40d) at both ends, when viewed in its axial direction, through which windows the test liquid in the cuvette is optically measured.

Figure 10A:
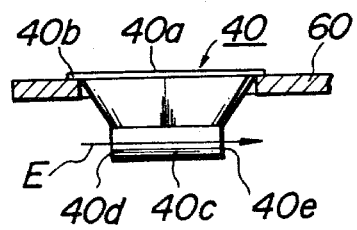
FIGS. 10a and 10b are side views illustrating a manner of holding the cuvette of FIG. 9.
Figure 10B:
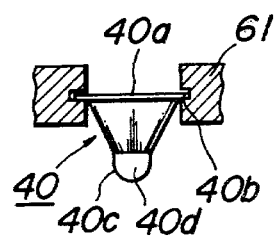

According to the above mentioned construction of the cuvette (40), since the opening (40a) (receiving port) is wide, it is possible to easily deliver the sample and reagent without splashing them externally. Further, the amount of test liquid is sufficient to fill the semi-cylindrical bottom portion (45c), and thus the analysis can be effected with very small amounts of sample and reagent. Moreover, since a measurement axis extends in a longitudinal direction of the cuvette and thus, is sufficiently long, it is possible to carry out the analysis with very high sensitivity. Since the side wall is tapered from the opening (40a) to the bottom (40c), and the flange (40b) is provided around the opening, the cuvette may be simply secured to the cuvette feed mechanism (35) and precision measuring section (48) in a manner shown in FIGS. 10a and 10b. That is, the flange (40b) may be placed on a holding member (60) as illustrated in FIG. 10a, or may be detachably inserted into recesses formed in a holding member (61) as depicted in FIG. 10b.

In this manner, the cuvette (40) may be simply supported by the holding member without making the measuring windows (40d) contact the holding member (60 or 61), and thus the measuring windows can be protected against injury. In FIG. 10a, an arrow (e) denotes the optical measuring axis. Further, the cuvette (40) may be formed by molding of a transparent material, and thus its mechanical strength can be made high.

FIGS. 11a and 11b are plan and side views, respectively, of an embodiment of a detachable holding mechanism for cuvette feed mechanism (35). The mechanism comprises a rotating member (35a) to which a pin (62) is secured. A pair of levers (63a and 63b) are journaled to pin 62 at their one ends, while the other ends serve to hold flange 40b of cuvette 40. In levers 63a and 63b are formed guide holes, 64a and 64b, respectively, and an operational level (65) extends through these holes, one end of which is secured to member 35a by means of a coiled spring (66) which pulls the level (65) in the proper direction (as shown in FIG. 11b) so that the free ends of levers 63a and 63b come near to each other so as to clamp the cuvette (40) therebetween. At each of the lag phase monitoring positions along the reaction line, is provided a motor (67), to the driving shaft of which is secured an eccentric cam (68) which can be engaged with the other end of operational lever 65.

By means of the above described holding mechanism, the cuvette (40) can be effectively supported and fed with its flange (40b) being supported by levers 63a and 63b. When the cuvette (40) in the lag phase monitoring position is ready to be lowered into the precision measurement section, motor 67 is energized to rotate the cam (68) which moves lever 65 against the force of spring 66 to open levers 63a and 63b. Then the cuvette (40) falls positively into the desired precision measuring position.

It should be noted that a mechanism for detachably holding a cuvette at each measuring position of the precision measurement section (48) may be constructed in the manner explained above.

Next a reagent cassette for holding the various reagent bottles and an associated cassette holder will be explained. FIG. 12 is a perspective view showing an embodiment of the cassette holder (32), and FIG. 13 is a perspective view illustrating an embodiment of the reagent cassette which may be removably installed in container 32. In this embodiment, the reagent cassette is reciprocally moved in a linear fashion within container 32 so as to index a given reagent bottle containing a desired reagent into the aspiration position corresponding to a desired reagent delivery pump. The cassette holder (32) comprises a rectangular box (70), a plurality of rollers (71) arranged at upper peripheries of the major side walls of the box, a slide member (73) having a rack gear secured so as to be able to move in a longitudinal direction along a guide slot (72), and a stepping motor (74) having coupled therewith a pinion gear for reciprocating arm (73). The reagent cassette may be clamped between arms 73a and 73b of slide member 73, and thus is reciprocated in the longitudinal direction together with member 73. The reagent cassette (75) comprises a box-shaped main body (76) with flanges 77a and 77b which slide on rollers 71. Inside the main body (76) are formed partitions (78) for placing a plurality of reagent bottles (79), arranged side by side in the direction of movement. The cassette (75) further comprises handles 80a and 80b.

As explained above, a plurality of reagent bottles (79) are removably installed in reagent cassette 75, and the cassette is then detachably installed in cassette holder 32. Therefore, a plurality of reagent bottles can be simultaneously handled and thus reagent choice operations are very simple. Further, a plurality of reagents can be stored in a separate refrigerator together with a cassette. Moreover, the reagent bottles (79) are removable from the cassette (75), making adjustment or addition of reagent easily effected. Since reagent cassette 75 is reciprocated linearly in holder 32, the driving mechanism can be made simple, and a detachable coupling mechanism between the driving mechanism and the cassette (75) can also be simply constructed.

In the reagent cassette, the reagent bottles may be arranged in random order, provided that an identification mark is applied to each reagent bottle, and a device for reading this mark is provided in connection with the cassette.

Figure 14:
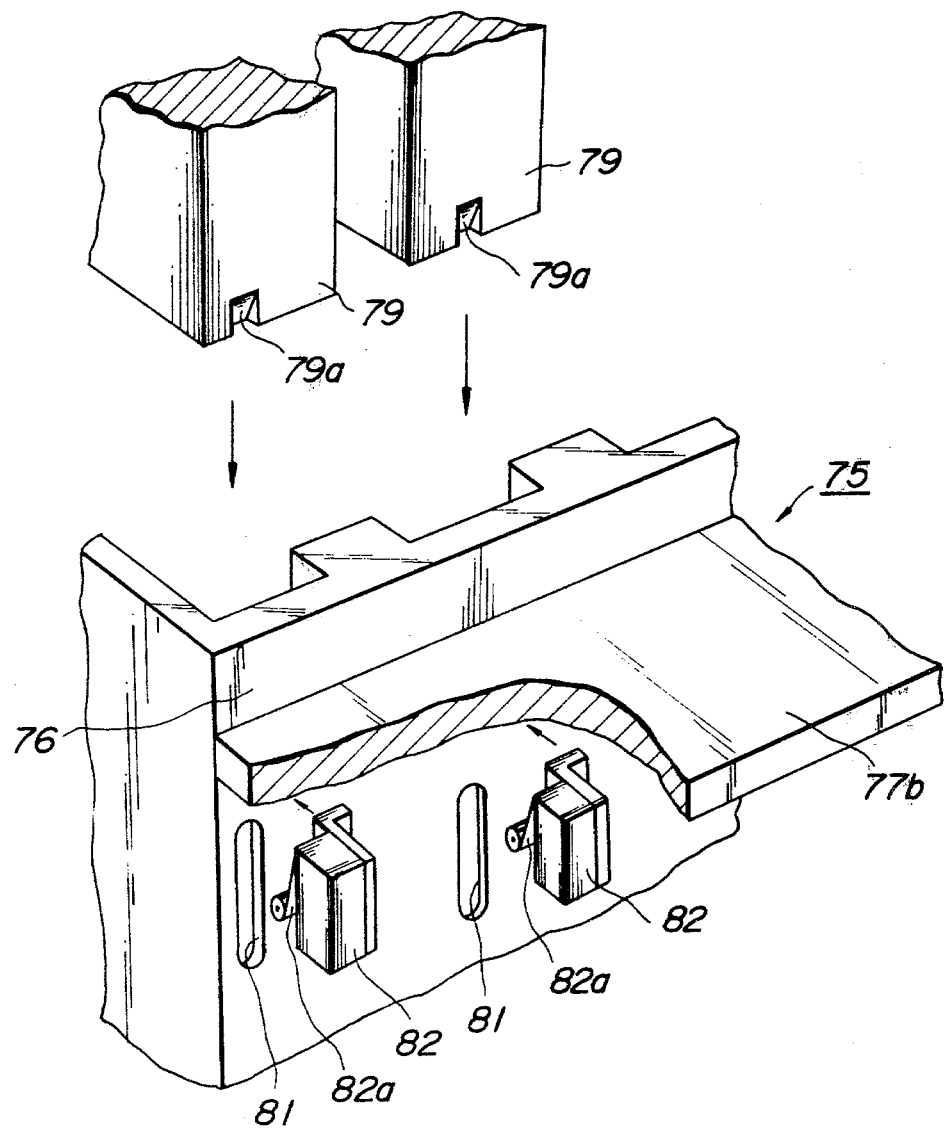
FIG. 14 is a perspective view showing an embodiment of a mechanism for avoiding mis-insertion of the reagent bottle into its cassette.

However, in an embodiment shown in FIG. 14, the order of arrangement of the reagent bottles in the cassette has been previously determined so as to minimize the total traveling distance of the cassette in accordance with the measurement frequencies of test items. In order to ensure that a given reagent bottle can be installed at a desired position in the cassette (75), the bottles (79) have formed at their bottoms, notches (79a). Elongated holes (81) are formed in a side wall of the main body (76) of the cassette, through which holes, actuators (82a) of microswitches (82) are projected inwardly. The actuators are so arranged that each actuator (82a) faces a respective notch (79a). The actuator is driven when any reagent bottle other than the predetermined one is inserted into the cassette (75) and an alarm is generated. If the width of the side wall is small, and a number of reagent bottles have to be installed in the cassette, it is possible to form two or more notches. It is further possible to use detecting means other than microswitches e.g. photoelectric detectors or magnetic detectors.

In order to maximize the operational efficiency of this analyzing apparatus in which several reagents, selected from a number of reagents, are delivered by a single delivery pump, it is preferably to effect the delivery of reagents in such an order that the total traveling distance of the cassette is minimized.

Figure 15:
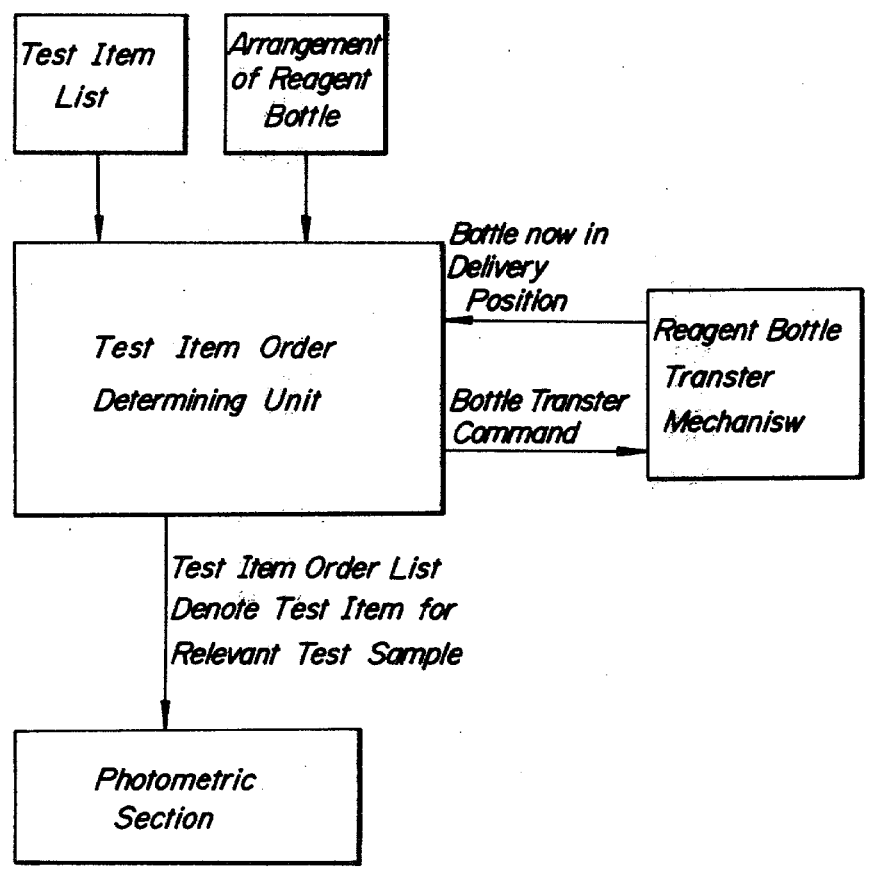
FIG. 15 is a block diagram showing a manner of controlling a reagent-feed mechanism for minimizing a total travelling distance of the reagent cassette.

As illustrated in FIG. 15, information about the arrangement of reagent bottles in the cassette has been previously stored in a test item order determining unit. Upon initiation of measurement for a particular test item, test item data to be effected for the relevant test item is supplied from a memory to the test item order determining unit, to which is also supplied information about a particular reagent bottle which is now in the reagent aspiration position in the reagent bottle transfer device. In the determining unit, the test item order is determined on the basis of these three pieces of information in such a manner that the traveling distance of the cassette in its holder can be minimized, and a list for denoting the determined test item order is formed. In accordance with this list, the order determining unit controls the successive alignment of reagent bottles with the reagent aspiration station in a sequence so as to insure the optimum economy of movement on the part of the cassette. At the time the list is generated, the list is also supplied to the photometric section, so as to provide the photometric section with test item data relevant to the photometer's responsibilities, for example, the overall sequence of test items and samples on the turntable.

Figure 16:
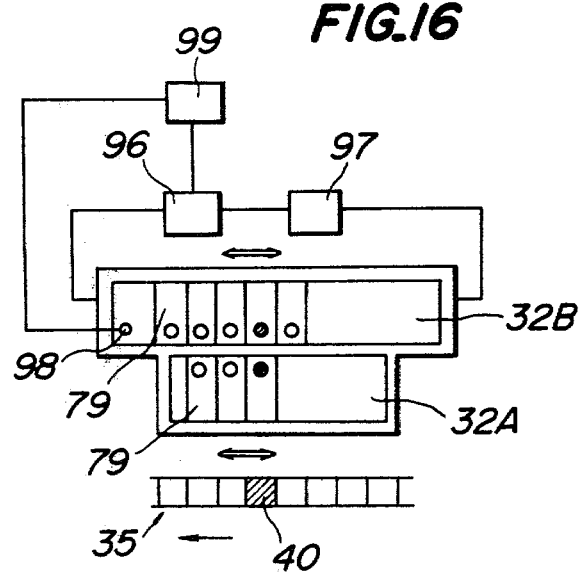
FIG. 16 is a schematic view illustrating an embodiment of the cassette holder comprising separate refrigerator and room temperature portion.
Figure 17:
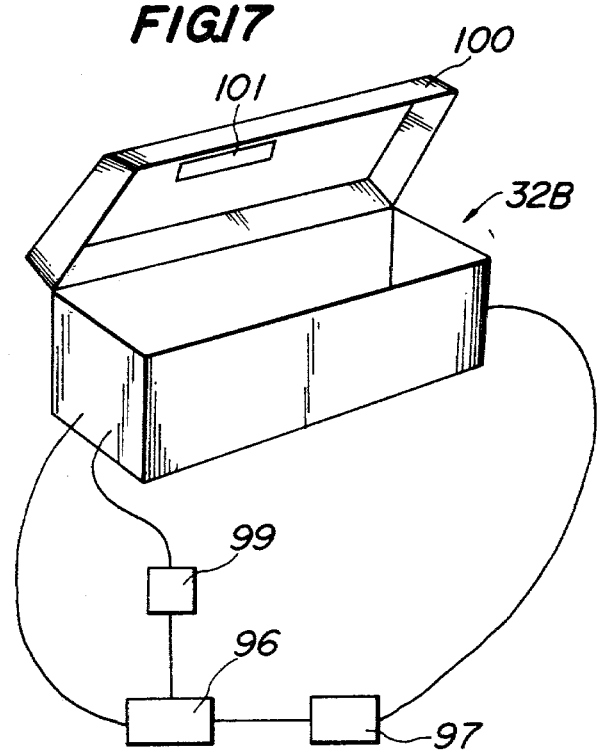
FIG. 17 is a perspective view showing an embodiment of the refrigerator in FIG. 16.
Figure 18:
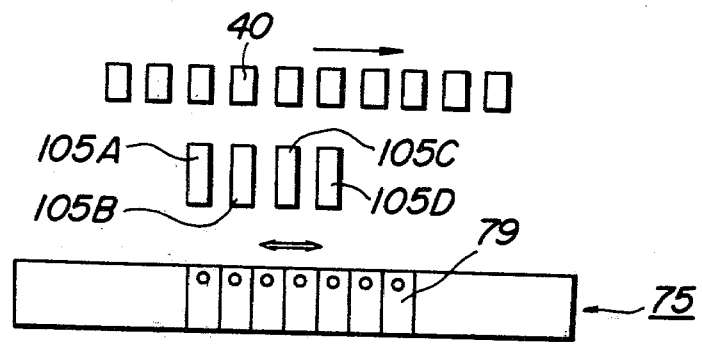
FIG. 18 is a schematic view explaining a delivery operation of the reagent delivery mechanism shown in FIG. 5.

In the above embodiment, all the reagent bottles are arranged in refrigerator 33 in order to avoid an alteration or deterioration of the reagents. However, some reagents might precipitate under a low temperature and thus should not be stored in the refrigerator. In such a case, as shown in FIG. 16, the cassette holder (32) is divided into two portions, 32a and 32b, one of which (32a) is kept at room temperature, and reagents which should not be stored at low temperatures are installed in this portion (32a). The other portion (32b) is connected to refrigeration machine 96, and blower 97, to form a closed loop. The operation of refrigeration machine 96 is controlled by a temperature-detecting element (98) in holder 32b, and a control circuit (99) which receives the output signal from temperature detector 98. It should be noted that the cassette shown in FIGS. 13 and 14 may be installed in portions 32a and 32b. In order to prevent the escape of cool air from refrigerator portion 32b, portion 32b comprises a lid (100) (illustrated in FIG. 17). A small aperture (101) is formed in the lid at a position corresponding to the aspiration position so that a fluid dispensing probe can be inserted into, and retracted from, portion 32b through hole 101. The fluid(s) which is (are) used to calibrate the apparatus is (are) preferably stored in refrigerator portion (32b).

Next the sample and reagent delivery mechanisms will be explained. They may have substantially identical construction and thus, only the reagent delivery mechanism will be explained herein below.

The reagent delivery mechanism (38) comprises four reagent delivery pumps connected to different diluents and/or buffer solutions. Each pump can deliver, selectively, any one of a plurality of different reagents. When a cuvette (40) is transported to a delivery position corresponding to any one of pumps 105a to 105d, for example 105a, and the reagent to be delivered to this cuvette is that which should be diluted by a diluent connected to this pump (105a), the related reagent bottle (79) is fed to a position corresponding to pump 105a, and then a given amount of the desired reagent is delivered into the cuvette (40) by the pump (105a). On the contrary, if the reagent to be delivered to this cuvette is that which should be diluted by a diluent connected to pump 105c, after the cuvette advances by two more steps, then at this position the desired reagent is delivered into the cuvette (40) by pump 105c.

According to the above explained reagent delivery mechanism, since diluents or buffer solutions which are optimum for particular reagents can be used, the reagents can be maintained in a stable condition for a longer time and the number of possible test items can be increased due to increased availability of reagent storage space. For some reagents, it is preferable to effect storage and/or delivery thereof in several containers and/or operations in order to arrange storage conditions to prolong the stable life time of reagents. In such a case, the same reagent may be delivered into the same cuvette by a succession of pumps (105a to 105d) at successive steps.

In the reagent delivery mechanism explained above, each pump can deliver a plurality of different reagents and thus each pump delivers the reagent drawn into its probe in a discrete delivery manner.

In this embodiment, use is made of reagents of high concentration and the reagents are jetted into cuvettes from the probes together with appropriate diluent(s). By utilizing this construction, the whole apparatus can be made small in size, and contamination between the different reagents can be avoided because the inside of probe is washed by the diluent(s). Since diluent(s) is/are heated to a temperature near the reaction temperature, the temperaure of the test liquid can be rapidly increased, and the reaction time can be shortened, even if refrigerated reagent is used and the reaction is carried out in a temperature-controlled incubation environment having a low thermal efficiency, such as an air bath. Further, if the diluent is the same liquid as any required buffer solutions, it is not necessary to provide separate delivery pumps for these liquids.

Figure 19:
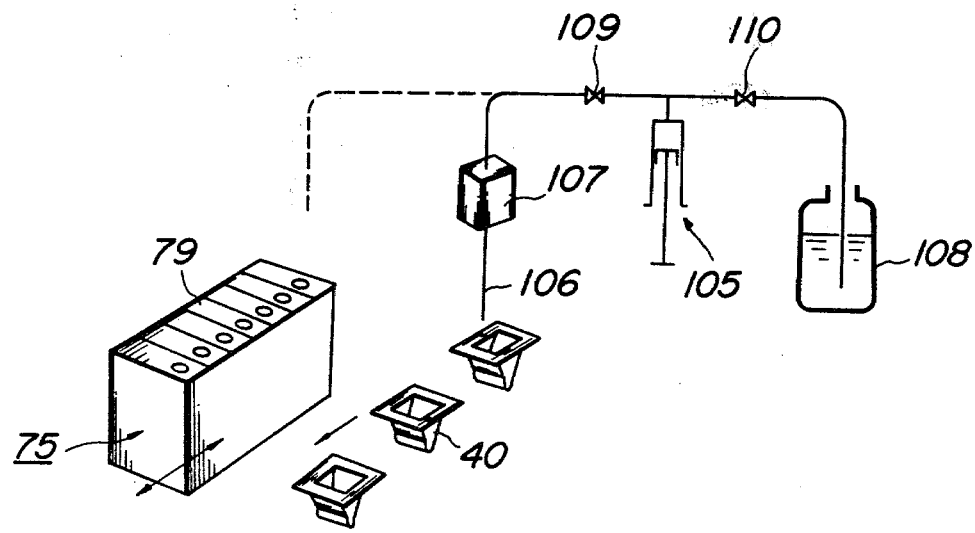
FIG. 19 is a schematic view showing an embodiment of the reagent delivery mechanism.

FIG. 19 is a schematic view illustrating an embodiment of the delivery pump. To delivery pump (105) (syringe) is connected a probe (106) which can be moved between the delivery position of the reaction line corresponding to this pump, and the drawing position above the reagent cassette (75). At first, the desired reagent bottle (79) in the cassette (75) is transported to a position just below the aspiration position of the probe (106) and the operation is carried out in accordance with an order illustrated in a following table. A preheating device (107) is provided to heat the diluent to a temperature near the desired reaction temperature and comprises a heater, a temperature sensor, and a temperature control circuit (not shown). The syringe (105) is connected to the probe (106) and a diluent bottle (108) via valves (109 and 110, respectively). In this embodiment, these valves are denoted as two-way valves, but they may be replaced by a single three-way valve. Sine these valves (109 and 110) are kept in contact with the diluent only, they do not require chemical resistance. However, in view of the very small amount of liquid to be delivered, it is desired that the volume inside the path be kept within very narrow and precise limits. To this end, it is preferable to construct the valves (109 and 110) by use of a rotary solenoid valve with a tapered cock.

The syringe and piston constructing the pump (105) do not require special chemical resistance properties because like the valves they contact only diluent liquid. In order to deliver different amounts of reagents by the same pump (105) the piston of the pump can be displaced by strokes of variable length by a pulse motor energized by an external signal. The diluent used may be made of a buffer solution as explained above or in some cases, use may be made of de-ionized or distilled water.

Operation steps of the reagent delivery pump will be denoted in the following table.

| STEP | POSITION OF PROBE (106) | VALVE (109) POSITION | VALVE (110) POSITION | SYRINGE (105) PISTON MOTION |
| --- | --- | --- | --- | --- |
| FORM AIR BUBBLE AT PROBE TIP | STAND BY POSITION (IN AIR) | OPEN | CLOSED | WITHDRAW SLIGHTLY |
| PROBE INTO REAGENT | STAND BY POSITION - IN REAGENT | CLOSED | CLOSED | NONE |
| ASPIRATE REAGENT | IN REAGENT | OPEN | CLOSED | WITHDRAW TO ASPIRATE REAGENT |
| TRANSPORT PROBE ABOVE CUVETTE | IN REAGENT - ABOVE CUVETTE | CLOSED | CLOSED | NONE |
| DELIVER REAGENT AND DILUENT INTO CUVETTE | ABOVE CUVETTE | OPEN | CLOSED | CLOSE TO DISPENSE |
| ASPIRATE DILUENT | ABOVE CUVETTE - | CLOSED | OPEN | WITHDRAW TO |

| STEP | POSITION OF PROBE (106) | VALVE (109) POSITION | VALVE (110) POSITION | SYRINGE (105) PISTON MOTION |
|---|---|---|---|---|
| | STAND-BY POSITION | | | ASPIRATE DILUENT |

In such a case, the same reagent or its component parts may be delivered into the same cuvette by a succession of pumps (105a to 105d) at successive steps.

In such a discrete delivering operation, it is quite important to assure whether a given amount of liquid has been aspirated or not. That is to say, if a serum, sample, or reagent is aspirated excessively or insufficiently, erroneous data would be obtained. Therefore, such a situation must be checked by some means.

Figure 20A:
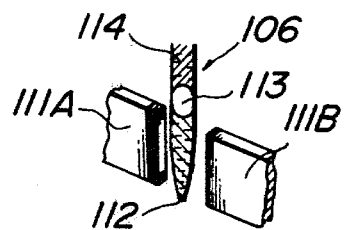
FIGS. 20a and 20b are perspective views and a graph, respectively, showing an embodiment of a liquid level detector of the reagent delivery mechanism, and the relationship between the amount of aspirated liquid and a detector output, respectively.
Figure 20B:
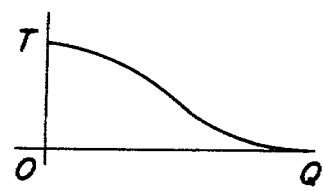

FIG. 20a is a schematic perspective view illustrating an embodiment of such means for detecting an amount of aspirated liquid. In this embodiment, the probe (106) is made of transparent material and a light-emitting element (111a), and a light-receiving element (111b), are arranged on opposite sides of the probe (106). In the probe (106), there is a liquid (112) such as a reagent or sample, an air layer (113) and a diluent (114), these materials having different absorptions. Therefore, a transmittivity, T, represented by an output from the light-receiving element (111b) changes as shown in FIG. 20b, depending upon a volume, Q, of the aspirated liquid (112). From this output, T, it is possible to detect whether or not a correct amount of liquid has been drawn into the probe.

Figure 21A:
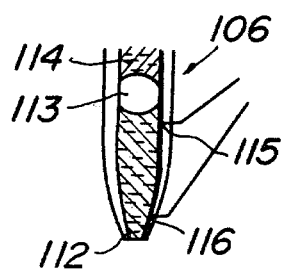
FIGS. 21a and 21b are a cross-sectional view and a graph showing another embodiment of the liquid level detector.
Figure 21B:
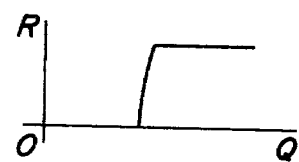

In an embodiment shown in FIG. 21a, a pair of electrodes (115 and 116) are arranged in the probe (106) with interposed a given distance therebetween. When a correct amount of liquid (112) has been aspirated into the probe, these electrodes (115 and 116) are conductively connected to each other via the electrically-conductive liquid so as to identify the correct amount of liquid. FIG. 21b illustrates a characteristic curve denoting a relation between the amount of aspirated liquid, q, and a resistance value, r, between the electrodes.

Figure 22A:
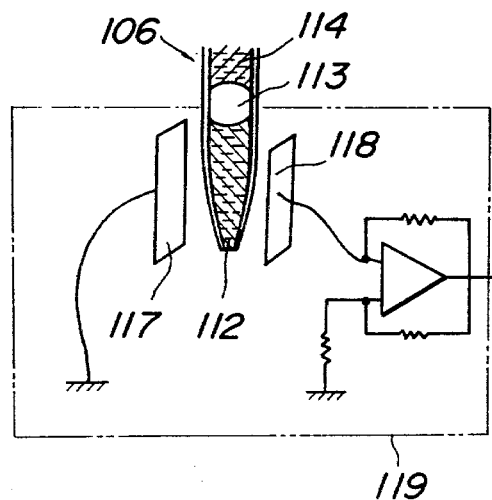
FIGS. 22a and 22b show still another embodiment of the liquid level detector.
Figure 22B:
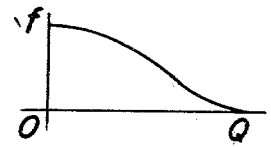

In another embodiment illustrated in FIG. 22a, a pair of plate-shaped electrodes (117 and 118) are arranged on either side of the probe (106) so as to form a capacitor. The capacitances between plates 117 and 118 will be a function of the liquid level in the probe (106). The capacitor is connected to a CR oscillator which will change frequency as capacitance changes. Liquid level in probe 106 will now be determined by frequency of CR oscillator. The output frequency of the oscillator, F, varies as a function of the amount, q, of the liquid (112) (see FIG. 22b). The output signal is counted by a counter (120) and an output from the counter is supplied to a discrimination circuit (121) to determine whether the amount, q, of the aspirated liquid (112) is correct or not.

When the reagent is aspirated by the reagent delivery probe which is immerse in the reagent as explained above, it is preferable to detect the level of the reagent in the bottle so as to control the depth of that portion of the probe which is immerse in the reagent.

FIG. 23 is a perspective view showing schematically an embodiment of such a liquid level detector. In this embodiment, the reagent bottle (79) is made of transparent material and a light-emitting device (130) and a light-receiving device (131) are arranged on opposite sides of the bottle (79). These devices comprise a plurality of light-emitting and receiving elements, respectively, arranged side by side in the vertical direction, and the liquid in the bottle (79) can be detected by output signals from these light-receiving elements. With the aid of these signals, the immersed depth or the probe (106) of the reagent delivery pump (105) can be controlled in a desired manner.

By the above explained measure, it is possible to draw positively a given amount of reagent while inserting the probe (106) into the reagent only to the minimum required depth and thus, the amount of reagent adhering to the outer wall of the probe can be minimized. Therefore, the tip of the probe can be easily and positively washed, and any contamination between the reagents can be effectively eliminated.

The liquid level detector may be constructed as illustrated in FIG. 24. In this embodiment, a holder (132) is secured to the probe (106) and a light-emitting element (133) and a light-receiving element (129) are provided at respective ends of arms of the holder (134). The reagent bottle (79) is made of transparent material. By lowering the holder (132) together with the probe (106), the liquid level of the reagent in the bottle (79) can be photoelectrically detected.

Figure 25:
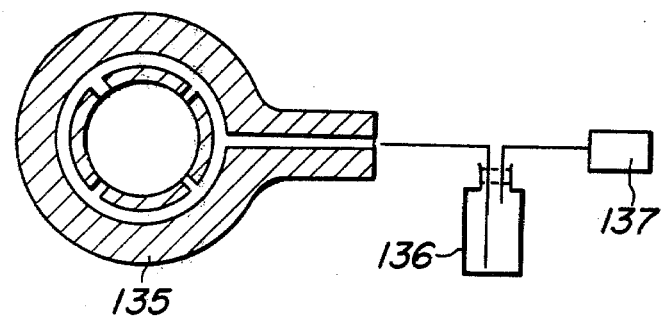
FIG. 25 is a schematic view showing an embodiment of a probe washing device.

Next, a device for cleaning the probe of a reagent delivery pump will be explained. FIG. 25 is a schematic cross section illustrating an embodiment of such a cleaning device. In this embodiment, a ring (135) having a plurality of openings in its inner wall is connected through a waste liquid bottle (136) to a vacuum pump (137). The probe is inserted into the ring (135) and the pump (137) is energized to aspirate liquid adhering to the outer surface of the probe into the bottle (136).

Figure 26:
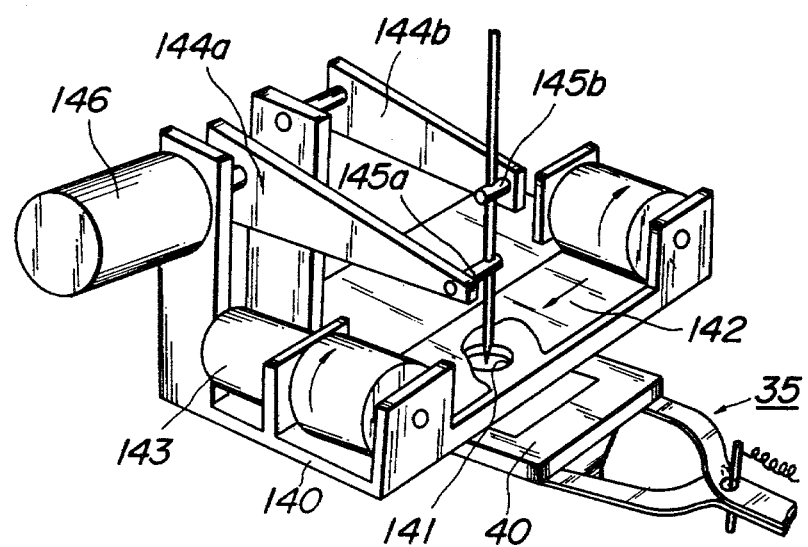
FIG. 26 is a perspective view depicting another embodiment of the washing device.

FIG. 26 is a perspective view illustrating another embodiment of the cleaning device. In this embodiment, by piercing the probe through a blotter, a reagent on the outer surface of the probe can be removed. To this end, a supporting plate (140) is arranged above the reaction line of the cuvette feed mechanism (35) in parallel with the reaction line. The supporting plate (140) has formed therein an opening (141) for passing the probe, and a blotter (142) is passed through the opening. The blotter (142) is wound onto a roll which is rotatably supported at one end of the plate (140). At the other end of the plate, a motor (143) is provided which takes up the blotter (142). It should be noted that a suitable load may be applied to the blotter roll so as to avoid looseness of the blotter. Upon delivering reagent, the probe (106) is inserted into the cuvette (40) on the reaction line through the blotter (142) and the aperture (141).

Figure 27A:
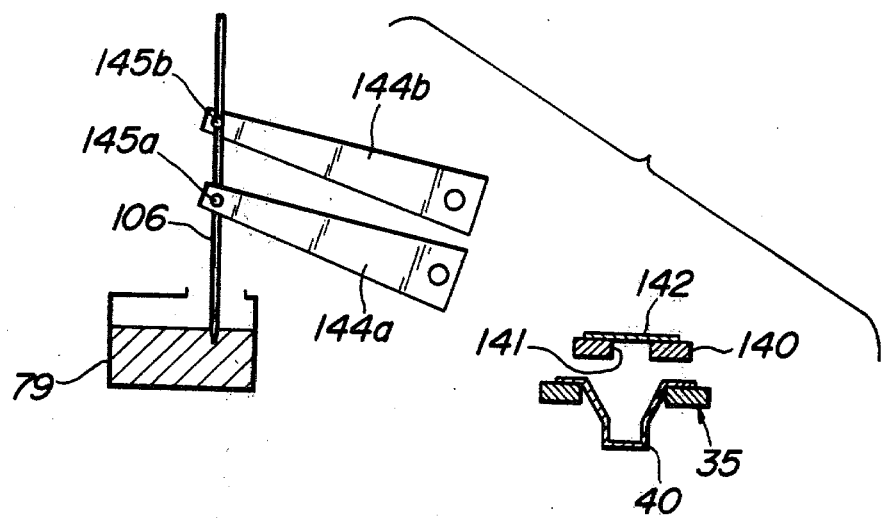
FIGS. 27a and 27b are schematic views for explaining the operation of the washing device shown in FIG. 26.
Figure 27B:
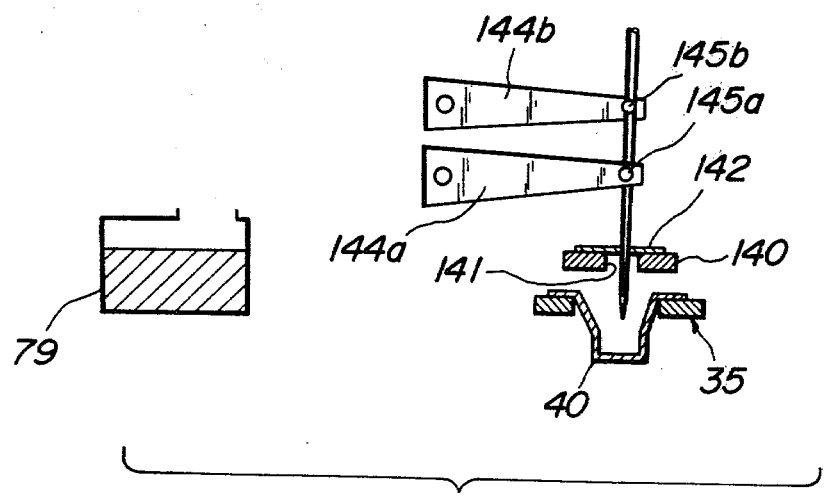

In this embodiment, a pair of arms (144a and 144b) are rotatably journaled to the supporting plate (140) and the probe (106) is rotatably supported at the free ends of the arms (144a and 144b) by means of pins (145a and 145b). To one of the arms (144a) is coupled a motor (146). The probe (106) can move between the arms (144a and 144b) into the reagent bottle (79) at the reagent aspirating position as shown in FIG. 27a, as well as into a position above the cuvette (40) through the blotter (142) and the opening (131), as illustrated in FIG. 27b. In this case, it is preferable to use the liquid level detector shown in FIG. 23.

In the above explained probe-washing device, since it is not necessary to use wash water, the construction becomes simple, and the probe (106) can be completely cleaned in conjunction with the liquid level detector.

The above explained probe-washing device and its transporting mechanism may also be applied to the probe of the sample delivery mechanism (39).

Next, a mechanism for disposing of cuvette and test liquids after photometric measurement will be explained. In this embodiment, waste liquids are not discharged from the analyzing apparatus. In the apparatus is provided a waste liquid handling mechanism for pre-treating chemical wastes before allowing their removal from the system so as to facilitate their disposal via environmentally responsible means.

Figure 28:
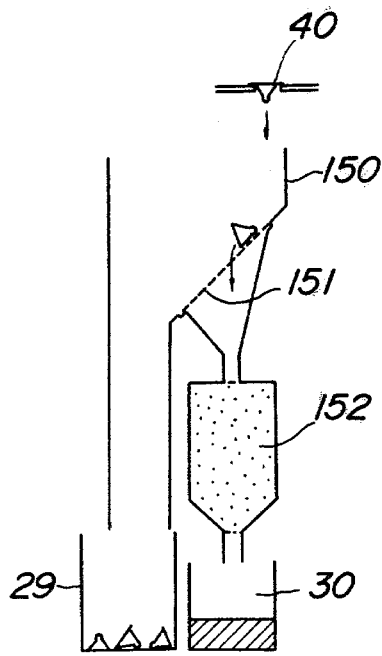
FIG. 28 is a schematic view showing an embodiment of a cuvette and liquid-discharging mechanism.

FIG. 28 is a schematic diagram showing an embodiment of such a disposal mechanism. The cuvette (40) is held by the supporting mechanism at each photometric position of the photometric measurement section. After measurement, the supporting mechanism is driven and the cuvette (40) is allowed to fall (as shown in FIG. 28 by an arrow). Underneath the cuvette (40) is arranged a duct (150) on which a mesh (151) is secured in an inclined fashion. The falling cuvette (40) strikes the mesh (151) and the contents of the cuvette is spilled into a neutralizing tank (152). The cuvette (40) slides downward on the mesh (151) until it is allowed to fall into a cuvette waste tank (29). In the neutralizing tank (152), the pH of the waste liquids is adjusted and noxious substances are removed. The filtrate is then passed to a waste liquid container (30). The neutralizing tank (152) is arranged in such a way as to be conveniently removable and if its treating ability is diminished, it may be regenerated or exchanged.

According to such a disposal mechanism, even if the waste liquid is temporarily stored in the container (30), annoying odors due to noxious substances would not be produced. Additionally, solid and liquid wastes are conveniently separated for disposal.

Figure 29:
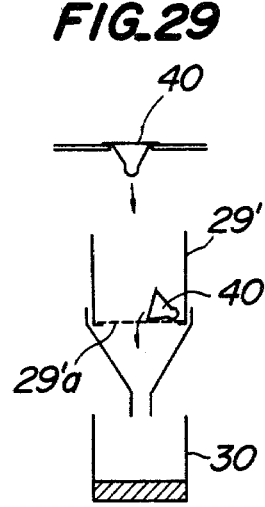
FIG. 29 is a schematic view showing another embodiment of the discharging device.
Figure 30:
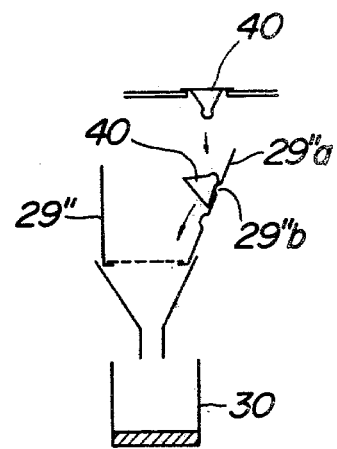
FIG. 30 is a schematic view showing still another embodiment of the discharging device.

FIGS. 29 and 30 are schematic views illustrating two other embodiments of a disposal mechanism. In FIG. 29, the cuvette (40) falling from the cuvette-supporting mechanism is received by a cuvette container (29') having secured a mesh (29a') at its bottom, and waste liquid is spilled into the container (30). Since the cuvette (40) has a shape as shown in FIG. 9, it rolls easily. Therefore, the liquid in the cuvette can be completely discharged. FIG. 30 shows the construction similar to that shown in FIG. 29 except that the falling cuvette (40) is positively turned on the inner wall of a cuvette container (29"). To this end, an inclined side wall (29a") of the container (29") is provided beneath the path of a falling cuvette and discontinuous projections (29b") are formed in the inner surface thereof.

According to such constructions similar to that in FIG. 28, solid and liquid wastes can be automatically separated to facilitate waste treatment and disposal.

Next, a control device for contolling the actions of each portion of the analyzing apparatus, introducing test item information, treating and displaying analyzed results and the like will be explained. As stated above, in the present embodiment, the control device is arranged apart from the analyzing apparatus itself. When the analyzing apparatus is separated from the control device; (a) When the analyzing apparatus is installed in a laboratory hospital or the like which has a computer of sufficient capacity, the analyzing apparatus can be controlled by supplying appropriate software to this computer; (b) In case a dedicated control device becomes out of order, by selectively connecting the analyzing apparatus with a transmission circuit, the analyzing apparatus can be operated by a back-up computer connected through the transmission circuit, and (c) In case an increase in productivity is necessary, a single control device can operate a plurality of analyzing apparatuses by adding one or more analyzing apparatuses to the analyzing apparatus already in operation.

Figure 31:
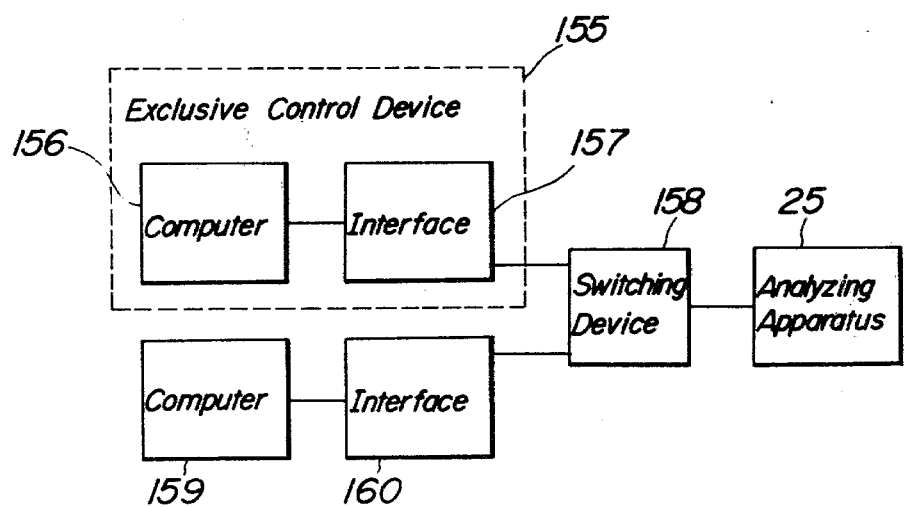
FIG. 31 is a block diagram showing a manner of connecting the automatic analyzing apparatus according to the invention to a remote computer installation.

The constructions for carrying out the above functions (a) to (c) will be explained in order. FIG. 31 is a block diagram showing the construction of an automatic analyzing apparatus according to the present invention, in which control of the automatic analyzing apparatus is switchable between a dedicated control device and some other computer system such as a lab's host computer system. A dedicated control device (155) comprises a computer (156) and an interface (157) and is connected to an analyzing apparatus (25) through a switching device (158). Further, an alternate computer (159) can be connected to the analyzing device (25) through an interface (160) and said switching device (158). In this manner, the switching device (158) is automatically or manually operated, and the analyzing apparatus (25) is connected to either the dedicated control device (155) or the alternate computer (159).

According to such construction, if the dedicated control device (155) is down, the alternate computer (159) can serve as back-up by operating the switching device (158), so that there is no interruption in analyzing operations. Further, the computer (159) can be operated without affecting the dedicated control device (155).

Figure 32:
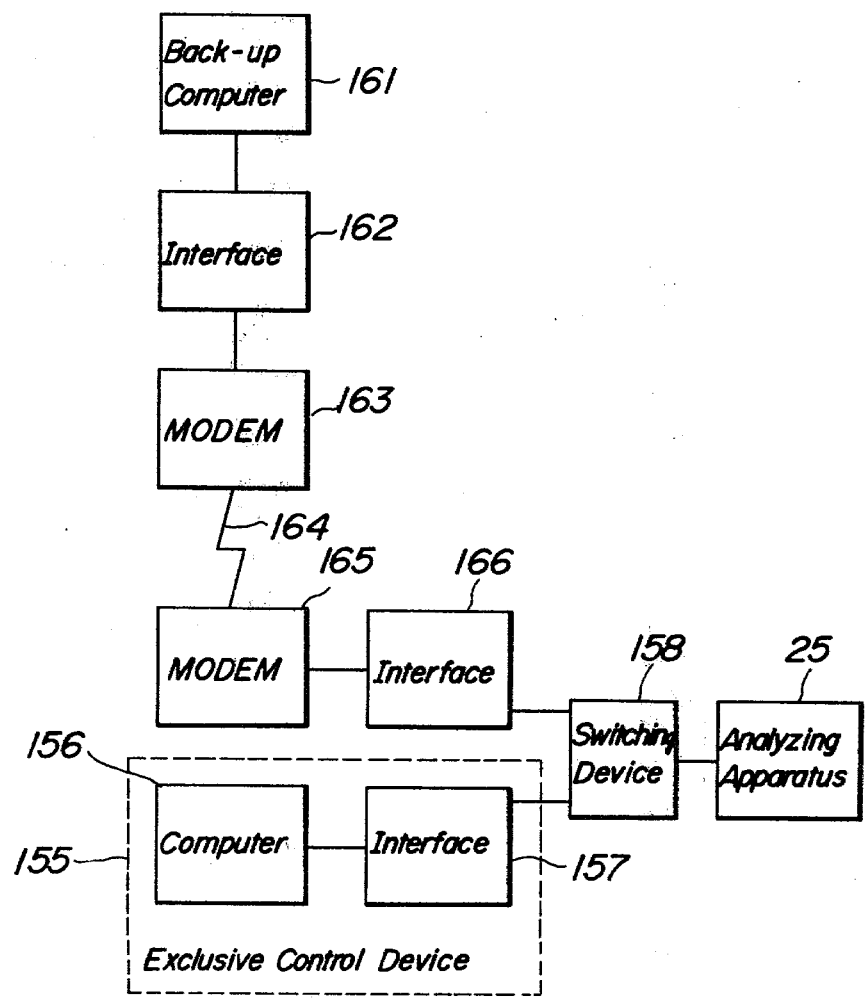
FIG. 32 is a block diagram illustrating a manner of coupling the apparatus according to the invention with a back-up computer through a communication line.

FIG. 32 is a block diagram showing another embodiment of the system, including the automatic analyzing apparatus according to the present invention, in which the automatic analyzing apparatus is connectable with a back-up computer through a communication line. Like numerals indicate like parts as shown in FIG. 31. A back-up computer (161) is connected to a communication line (164) through an interface (162) and a MODEM (163). This back-up computer (161), interface (162), and MODEM (163) are installed at a service company, maker or the like. On the side of the provisions provided with the analyzing apparatus (25), is provided a MODEM (165) connected to said communication line (164) and further connected to the switching device (158) through an interface (160). In this manner, the switching device (158) can be automatically or manually operated, and the analyzing apparatus (25) is then connected to either the back-up computer (16) or the dedicated control device (155).

According to such construction, as described above, even if the dedicated control device (155) becomes out-of-order, the back-up computer (161) can operate the analyzing apparatus (25) through the communication line (164) until repair is completed so that there is no prolonged interruption in analyzing operations.

Figure 33:
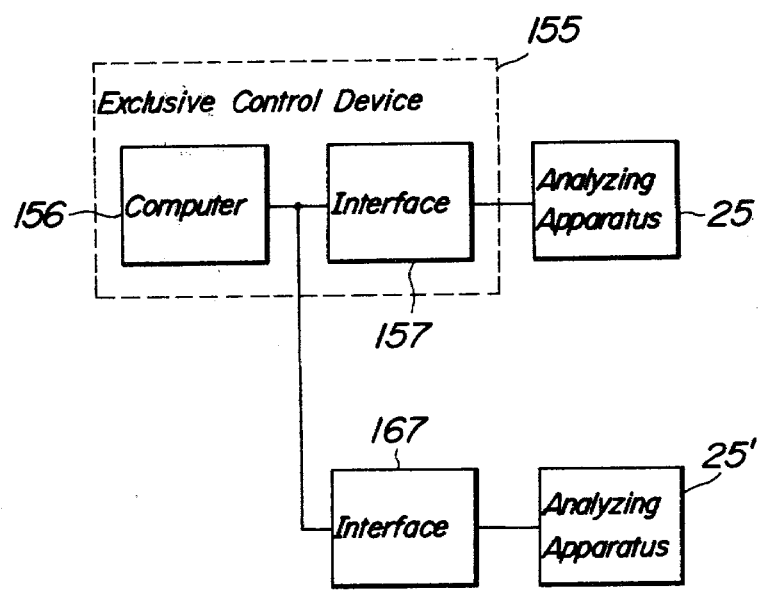
FIG. 33 is a block diagram showing a manner of controlling or operating a plurality of the analyzing apparatuses according to the invention by means of a single controlling unit.

FIG. 33 is a block diagram showing still another embodiment of the system comprising the automatic analyzing apparatus according to the present invention, in which one control device can operate a plurality of analyzing apparatus. In this embodiment, like numerals indicate like parts as shown in FIG. 31. In this embodiment, a computer (156) in one dedicated control device (155) can be connected to one analyzing apparatus (25) through an interface (157) as well as to an additional analyzing apparatus (25') through an interface (167).

According to such construction, a plurality of analyzing apparatuses (25, 25') can be controlled by the single control device (155) so that productivity can be increased expeditiously and economically.

A patient-data system for use with an automatic analyzing apparatus according to the present invention will be explained.

In a conventional automatic analyzing apparatus, a commonly used patient data system begins with a test requisition form which, in a clinical setting, is usually filled out by, or under the direction of, a given patient's attending physician. This filled-in requisition form includes the patient's name and/or an identifying number and the tests for which the sample must be analyzed as minimum information.

The various test requisition forms are used to prepare a loading list. The loading list describes each sample's identification (by name and/or number) and its position on the instrument's sampler and/or its place in the sample queing. Test results are generated in the same sequence as samples are introduced, and the relationship between test results and the corresponding patient can be determined from the loading list. The analytical results can be manually transferred to the requisition slip for use as the report form ultimately returned to the attending physician or; the patient identification information can be manually transferred to the standard instrument report form or; both the analytical results and the patient information can be manually transferred to yet another form to serve as the physician's report.

In such a patient data system, however, it is necessary to copy the analytical results and/or patient information. Further, in case of deleting or adding a sample, or inserting a stat (urgent) sample by squeezing it between samples, the relation between the analyzed results and the loading list changes and the following mistakes can occur.

1. Mistaken match of sample number to patient name.
2. Posting mistake of patient information and/or analytical results.
3. Mistaken match of sample aliquot to identification name and/or number.
4. Proper match of sample and identification number, but mistaken match to patient name.

Another common patient data system involves transferring patient data from the requisition form into a computer memory and printing it out together with analytical results. In this system, however, the patient information must be transferred manually by means of a keyboard, so that it is subject to a loading mistake. In yet another system, test item selection information is automatically loaded into a computer memory from a requisition card, but sample I.D. is manually collated with a patient, so that there is the possibility of a mistake similar to those described above.

Conventional automatic analyzing systems frequently include as part of the instrument report form some means for flagging or highlighting abnormal test results. Usually an expected range of values are predetermined and any test result outside this range of values is somehow flagged as 'abnormal' on the instrument report form. However, patient populations differing by such things as age, sex, or the like, will have different expected ranges. For improved diagnostic information, it would be more appropriate to compare a given patient's results against those of an appropriate population.

The patient data system for the automatic analyzing apparatus according to the present invention eliminates various inconveniences in the above described conventional data systems while improving upon the integrity of data by reducing opportunities for error to occur.

The data system of the present invention utilizes a copy of the physician's original requisition form to obtain pertinent patient data and test selection information. The same form is used to provide an inseparable link between patient name and sample number and to serve as the instrument report form which includes patient identification data, sample number, analytical results, population appropriate expected ranges, and abnormals flagging (when appropriate). As a result of this data system. The possibility for the above mentioned errors has been eliminated. In addition, this system reduces the amount of paper which must be handled and consumed since the present invention uses the original test requisition form as the report form.

Figure 34:
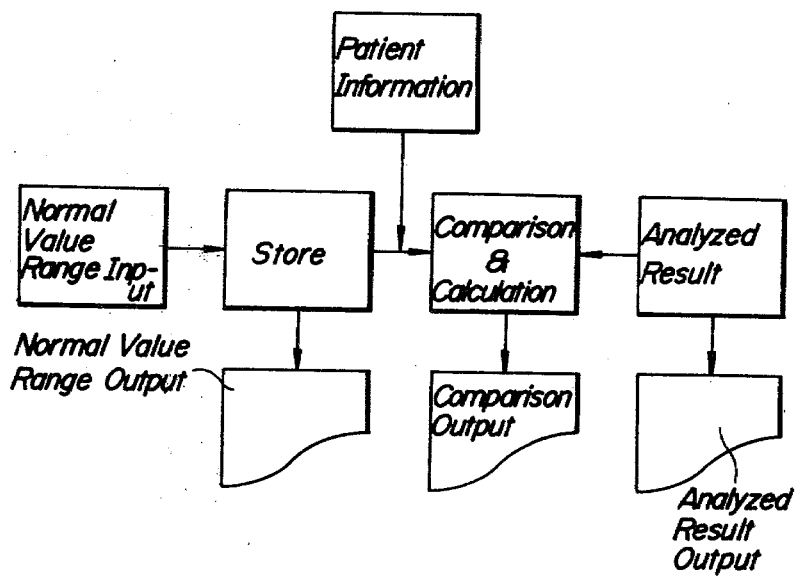
FIG. 34 is a flow chart showing an embodiment of a patient-data system using the apparatus according to the invention.
Figure 35:
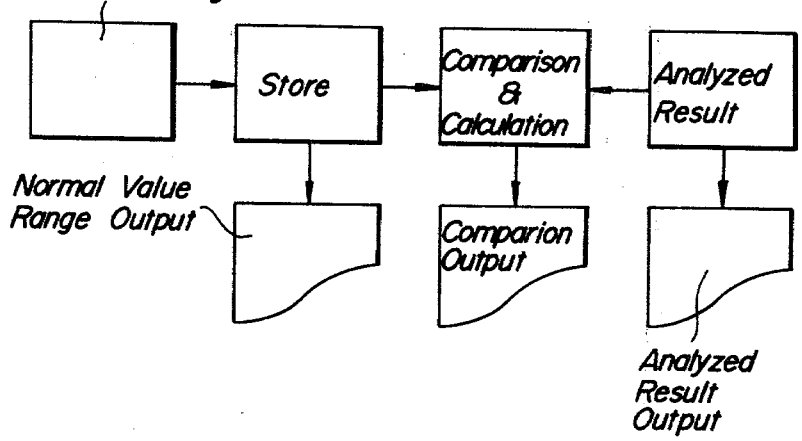
FIG. 35 is a flow chart showing another embodiment of the patient-data system.
Figure 36:
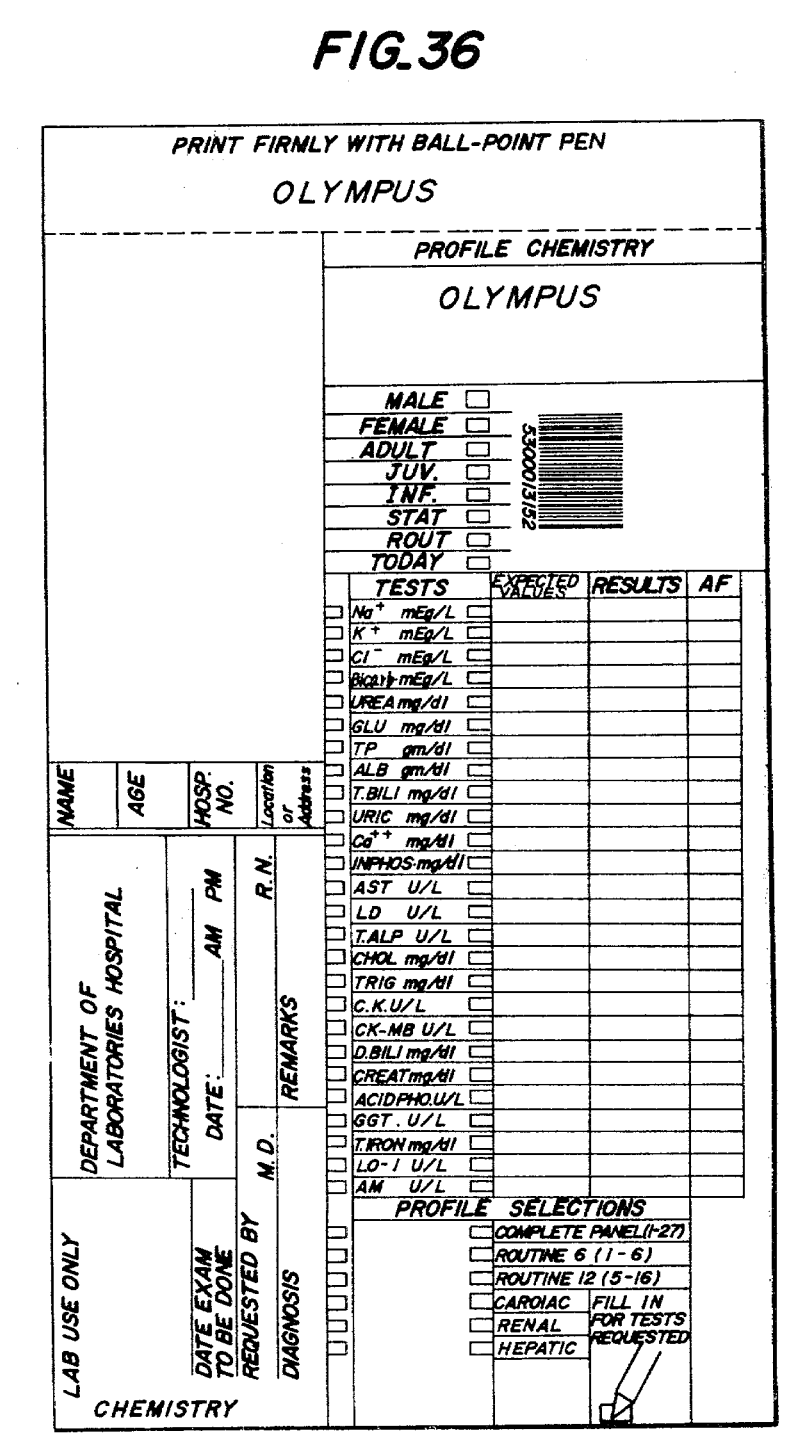

FIGS. 34 and 35 are flow charts of a patient data system of the automatic analyzing apparatus according to the present invention. FIG. 36 is a plan view showing a format of a patient card used in such system. The flow chart shown in FIG. 34 indicates that the various expected ranges by test item and population parameters (sex, age, medical prescription, and the like), have been previously stored in the analyzing apparatus and expected values corresponding to the patient's appropriate parameters are printed on the requisition/report form. On the requisition/report form, the analytical results and judgments obtained by comparing the analytical results against appropriate expected range values are also printed out. In the flow chart of FIG. 35, the patient information and the expected range values corresponding to the relevant patient have been previously recorded on the requisition/report form and the analytical results and judgments are subsequently printed on the form. In this case, the requisition/report form is fed through the reader/printer twice. During the first feed, the test item selection information and the patient's expected range population parameters corresponding to an identifying number are read out and appropriate expected ranges are printed on the form. As shown in FIG. 36, use is made of a bar code for the identifying number. When abnormal analytical values are detected, judgments are printed in an AF (Abnormal Flags) column with marks for indicating the direction of deviation from the expected range and an amount of abnormality (for example: the number of standard deviations the analytical result differs from the mean expected value.)

Figure 37:
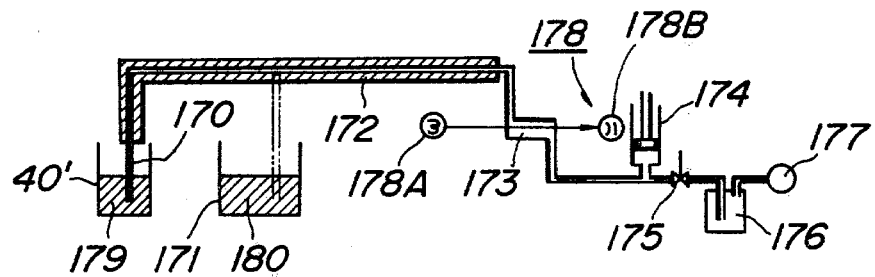
FIG. 37 is a schematic view showing another embodiment of the apparatus according to the invention, in which only a test liquid is supplied from a reaction line to a precise measuring section.

It should be noted that the present invention is not limited to the embodiments mentioned above, but many modifications can be conceived within the scope of the invention. For instance, in the above embodiment, the lag phase is monitored before the precision photometric measurement of the linear phase, but an end point may be monitored by the lag phase monitoring section, and after the end point is detected, a precision measurement may be carried out. In this embodiment, after the detection of the end of the lag phase by the monitoring section, the test liquid is removed from the reaction line together with the cuvette and then the precision measurement is effected. However, as shown in FIG. 37, it is possible to transport only the test liquid from the reaction line to the precision measuring section. In FIG. 37, an aspiration probe (170) is arranged so as to be movable between the cuvette (40') on the reaction line to a washing bottle (171). The probe (170) is connected to a syringe (174) through a heat-insulated tube (172) and a flow-type photometric cuvette (173). The syringe (174) is coupled to a suction pump (177) via a valve (175) and a waste liquid tank (176). A precision measuring photometer (178) is comprised of a light source (178a) and a photoelectric converter (178b) arranged on opposite sides of photometric cuvette 173. Initially, valve 175 is closed and probe 170 is immersed into the cuvette (40') on the reaction line, the contents of the cuvette having been previously detected to be in the linear phase, and syringe 174 is operated to draw a given amount of the test liquid (179). Then, the probe (170) is moved into the washing bottle (171) and the syringe (174) is operated again to aspirate wash water (180) so that the previously aspirated test liquid is fed into the photometric cuvette (173). Then the aspiration of wash water (180) is halted and measurement is effected by means of photometer 178 while the test liquid is stationary in cuvette 173. After measurement, valve 175 is opened and the pump (177) is energized to discharge the test liquid and wash water aspirated into tank 176. During this operation, the syringe (174) is returned to its initial position. Since aspiration probe 170 and photometric cuvette 173 are washed with water after measurement, contamination cannot occur. The aspiration and measurement may also be carried out in the manner described below. At first, valve 175 is closed and the syringe (174) is operated to draw test liquid (179) into cuvette 173, and measurement is effected. After measurement, valve 175 is opened and pump 177 is driven to aspirate the wash water (180). At the same time, syringe 174 is returned to the initial state. As above, measurement can be effected without any contamination.

Figure 38:
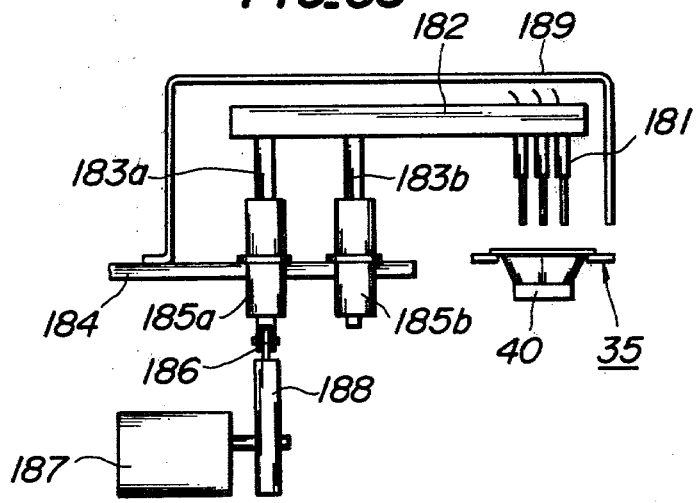
FIG. 38 is a schematic view showing an embodiment of an ion-concentration measuring device which may be installed in the apparatus according to the invention.

To improve upon the analytical capabilities of the present invention as described above, it is further possible to provide an ion activity measuring device at any position on the reaction line after reagent delivery so as to measure concentrations of ions of such potential test items as Na, K, Cl, etc. FIG. 38 illustrates an embodiment of such a device. In this embodiment, a plurality of ion selective electrodes (181) are immersed in the cuvette (40, set in the cuvette-feed mechanism (35) (reaction line) to measure the ion concentration. These electrodes (181) are secured to one end of an arm (182), to the other end of which is secured a pair of guide rods (183a and 183b), which are inserted so as to allow movement in sleeves 185a and 185b, respectively, provided in a supporting plate (184). At the free end of the guide rod (183a) is journaled a roller (186), which is urged against an eccentric cam (188) which is secured to the driving shaft of a motor (187). In order to avoid dust contamination, the ion activity measuring device is protected by a cover (189). As the cam (188) is rotated by the motor (187), the arm (182) moves up and down vertically, while it remains horizontal owing to the sleeves (185a) and (185b). When the arm (182) is lowered, the ion selective electrodes (181) are immersed in the test liquid in the cuvette (40) to measure simultaneously various ion activities.

Figure 39:
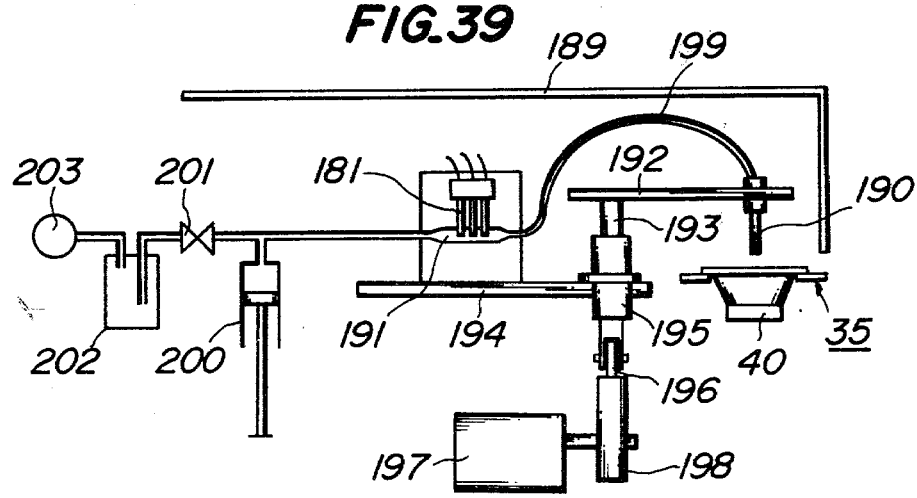
FIG. 39 is a schematic view showing another embodiment of the ion-concentration measuring device.

FIG. 39 is a schematic view illustrating another embodiment of the ion activity measuring apparatus. In this embodiment, the test liquid in the cuvette (40) is aspirated by a nozzle (190) into a flow cell (191) in which various kinds of ions can be detected and measured. The nozzle (190) is secured to one end of an arm (192), the other end of which is secured to a guide rod (193). The guide rod (193) is inserted so as to allow movement in a sleeve (195) which is secured to a supporting plate (194). A roller (196) is secured so as to allow rotation at one end of the guide rod (193), and is urged against an eccentric cam (198) which is secured to the driving shaft of a motor (197). When the cam (198) is rotated by the motor (197), the nozzle (190) is immersed into the test liquid in the cuvette (40). The nozzle (190) is connected to a syringe (200) through a flexible tube (199) and a flow cell (191) and to a suction pump (203) through a valve (201) and a waste liquid tank (202). The ion selective electrodes (181) are arranged in such a manner that their measuring surfaces project into the flow cell (191). In order to protect the apparatus against dust, a cover (189) is provided. At first, valve 201 is closed and the nozzle (190) is immersed into the test liquid in the cuvette (40) on the reaction line by energizing the motor (197). Then, the syringe (200) is operated to aspirate a desired amount of the test liquid in the cuvette (40) into the flow cell (191). Under such conditions, concentrations of various ions in the test liquid are quantitated by the ion selective electrodes (181). After measurement, the valve (201) is opened and the pump (203) is energized to discharge the test liquid into the tank (202) and the syringe (200) is returned to its initial position.

Figure 40:
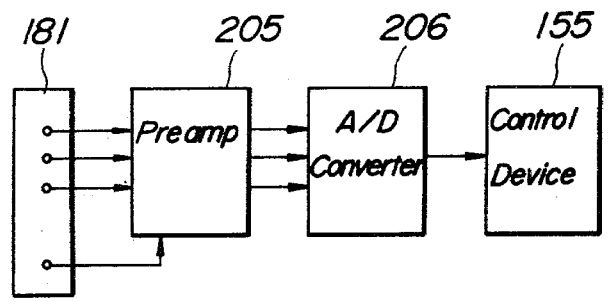
FIG. 40 is a block diagram showing an embodiment of a signal processing circuit of the ion-concentration measuring devices shown in FIGS. 38 and 39.

FIG. 40 is a block diagram showing an embodiment of a signal-processing circuit of the above mentioned ion activity measuring device. Output signals from the ion selective electrodes (181) are amplified by a preamplifier (205) and then are converted into a digital signal by an analog-digital convertor (206). The digital signal thus obtained is supplied to a control device (155) and is processed in a desired manner therein.

In the ion activity measuring device shown in FIGS. 38 and 39, a blotter may be arranged above the reaction line as illustrated in FIG. 26 and the ion selective electrodes (181) and the nozzle (190) may pierce the blotter. Alternately, a wash bottle may be arranged apart from the reaction line as depicted in FIG. 37 and the ion selective electrodes and the nozzle can be immersed in this bottle. In this manner, the ion selective electrodes and the nozzle can be cleaned so as to avoid any contamination between successive test liquids and thus very accurate measurement can be conducted.

Further, in the above embodiments, the measuring section (48) is so constructed so as to analyze test items in a test liquid by means of a standard photometric method, but use may be made of nephelometric and fluorometric methods in addition to the standard photometric method.

Figure 41:
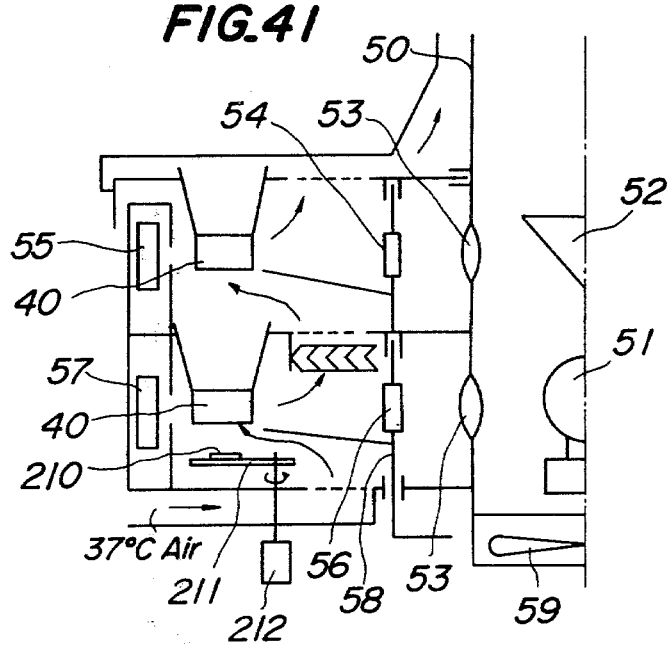
FIG. 41 is a cross section showing schematically an embodiment of a photometric section of the apparatus according to the invention, which can effect colorimetric nephelometric and fluorometric analyses.
Figure 42:
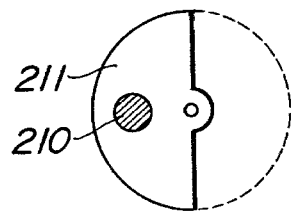
FIG. 42 is a plan view showing a holding plate for supporting a light-receiving element for scattered and fluorescent light.

In such a case, a light-receiving element (210) for receiving scattered or fluorescent light may be removably arranged underneath the cuvette (40) in the precision measuring position as shown in FIG. 41. The light-receiving element (210) is secured to a semi-circular supporting plate (211) (see FIG. 42) which is rotated by a motor (212). After measurement, motor (212) is driven so as to rotate element (210) and supporting plate (211) to remove them from a position beneath the cuvette (40) and then the cuvette (40) in the precision measuring position is dropped.

Figure 43:
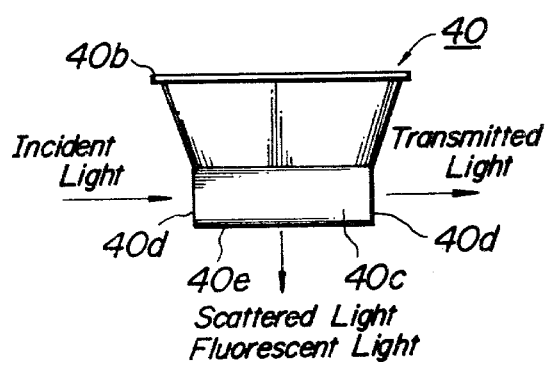
FIG. 43 is a schematic view showing an embodiment of a cuvette for use in measurement of transmitted, scattered and fluorescent light.

When effecting nephelometric and fluorometric analyses by receiving the scattered light or fluorescent light from the test liquid, it is preferable to form the bottom portion (40c) of the cuvette (40) into a flat bottom (40e) instead of a semi-cylindrical bottom as shown in FIG. 43.

In this manner. It is possible to obtain a very useful automatic analyzing apparatus which can measure quite a large number of test items over a wide range by adding nephelometric and fluorometric analyzing capabilities.

In the above embodiment, for nephelometric and fluorometric analyses, use is made of a light-receiving element separate from that of the photometer, but a single, shared, light-receiving element may be used for transmitted light, scattered light and/or fluorescent light. FIGS. 44–47 show several embodiments of such an arrangement. In FIG. 44, a cuvette (40') is rotatably arranged. Initially, cuvette (40') is so arranged that incident light impinges vertically upon a transparent incident surface and the light passing through the cuvette is received by an element (215) so as to effect photometric analysis as shown in FIG. 44a. Then, the cuvette (40') is slightly rotated, as shown in FIG. 44b, so that the transmitted light deviates from the usual optical axis of element (215), and thus the scattered and/or fluorescent light impinges upon element (215). In this manner, nephelometric and fluorometric analyses can be carried out. In FIGS. 45 and 46, light-receiving element (215) is so arranged that it can receive scattered and fluorescent light and the transmitted light is directed to the element (215) via a rotating mirror (216). In FIG. 45, the scattered and fluorescent light from a side wall of the cuvette (40') impinges upon element (215) through a scattering element (217). In FIG. 46, the scattered or fluorescent light from the bottom of the cuvette (40') impinges upon element (215). In the case of photometric analysis, rotating mirror (216) is positioned as shown in the drawings, and transmitted light is received by element (215). During nephelometric or fluorometric analyses, the mirror (216) is rotated into a position shown by a dotted line and the scattered or fluorescent light selectively impinges upon element (215). In an embodiment shown in FIG. 47, the cuvette is so shaped that the photometric, nephelometric and/or fluorometric analyses can be effected by a common light-receiving element (215). As shown in FIG. 47a, in the case of photometric analysis, use is made of a cuvette (40') having transparent walls perpendicular to the incident light path, whereas in the case of nephelometric or fluorometric analyses, as shown in FIG. 47b, use is made of a cuvette (40") having a transparent wall inclined to the incident light path by 45°.

As explained above, by effecting the photometric, nephelometric and fluorometric analyses by means of a common light-receiving element, construction of the photometer can be made much simpler.

In the above embodiments, the reagent delivery mechanism (38) comprises four delivery pumps, but it is sufficient to provide only a single delivery pump in order to deliver, selectively, various kinds of reagents. Further, in the above embodiments, the reagent bottles (79) are installed in a linear fashion within the cassette (75) which is then moved in a linear fashion within the cassette holder, but it is also possible to arrange the various reagent bottles (79) in a cassette comprising a movable, endless belt, so as to index a desired reagent bottle to a given delivery position. Moreover, the reaction line may be arranged in a linear fashion rather than a circular fashion and further, a plurality of such reaction lines may be arranged in the apparatus.

What is claimed is:

1. An apparatus for effecting automatic analysis for sample liquids comprising:

means for successively feeding reaction vessels, each containing respective sample liquid to be analyzed, along a given reaction line;

means for delivering a given amount of a given reagent, corresponding to a test item to be measured, into a reaction vessel on the reaction line to form a test liquid which is a mixture of the sample liquid and reagent;

first photometering means arranged at a reaction-condition-monitoring-section, provided along the reaction line, for monitoring a reaction conditon of the test liquid in the vessel;

second photometering means arranged along the reaction line for effecting quantitative analysis for the given test item; and means for discharging the reaction vessels out of the reaction line after the quantitative analysis for the given test item has been done, the improvement comprising in said second photometering means having a plurality of measuring positions arranged in a precise photometering section which is provided separately from the reaction line, said discharging means being in the precise photometering section, and comprising further means for transporting the reaction vessel from the reaction-condition-monitoring-section into any desired measuring position in the precise photometering section after the test liquid contained in the relevant reaction vessel has been confirmed to reach a predetermined reaction condition.

2. An apparatus according to claim 1, wherein said transporting means comprises a device for feeding a reaction vessel having a test liquid contained therein.

3. An apparatus according to claim 1, wherein said precision photometry section is arranged beneath the reaction line, and said transporting means comprise means for dropping a reaction vessel, having a test liquid contained therein, into the precision photometry section.

4. An apparatus according to claim 3, wherein said second photometry means comprise a plurality of precision photometers arranged along the reaction line, and the reaction vessel is selectively dropped into a precision photometer which is not occupied by a previously introduced reaction vessel.

5. An apparatus according to claim 1, wherein said reagent delivering means is operated to deliver a given reagent (corresponding to a given test item) selected from a plurality of reagents, so that the apparatus is operated as a single-channel multiple test item analyzer.

6. An apparatus according to claim 5, wherein said second photometry means comprise a plurality of optical fibers having different transmission wavelengths, a given one of which is selectively inserted in an optical path of the second photometry means in dependence upon the test item to be analyzed.

7. An apparatus according to claim 6, wherein said reaction line is formed as a circle, said first photometry means comprise a plurality of photometers which are arranged along said circle, said second photometry means comprise also a plurality of precision photometers which are also arranged in a circular fashion beneath the circular reaction line, said second circle being concentric with said first circle, said plurality of optical filters are provided in a cylinder rotatably arranged about an axis which passes through the center of rotation of said circles, and said first and second photometry means comprise a single common light source emitting panchromatic light, and arranged at said center.

8. An apparatus according to claim 7, wherein the first photometry means further comprise a plurality of fixedly arranged filters.

9. An apparatus according to claim 7, wherein said light source is arranged in a cylinder having a top end exposed to the outside and a ventilating fan arranged at the bottom of the cylinder.

10. An apparatus according to claim 7, wherein an air stream of a given temperature is circulated through the monitoring and precision photometry sections so as to maintain the temperature of test liquids at a desired value.

11. An apparatus according to claim 1, further comprising
Sample feeding means for successively transporting sample cups to a sample-delivering section; and
Sample-delivering means provided at the sample delivering section, for delivering a given amount of each sample liquid into a respective reaction vessel.

12. An apparatus according to claim 11, wherein said sample feeding means comprise a rotating disc in the form of a sprocket wheel, successive sample cups being set in each of recesses of the sprocket wheel, and a sample carrier chain which can be detachably engaged with the sprocket wheel and can contain a number of sample cups.

13. An apparatus according to claim 1, wherein said reagent delivering means comprise a reagent cassette which is detachably set into the apparatus, and contains a plurality of reagent bottles containing different reagents, means for moving the reagent bottles past a reagent aspiration position, and a reagent delivery pump for aspirating into its probe a given amount of a given reagent, contained in the reagent bottle which is situated at the aspiration position, and discharging the aspirated reagent into a reaction vessel in which a given amount of sample liquid may already have been delivered.

14. An apparatus according to claim 13, wherein the reagent bottles contain reagents having higher than usual concentrations, and a given amount of a diluent, contained in a diluent bottle, is delivered into the reaction vessel.

15. An apparatus according to claim 14, wherein said reagent delivery pump is also coupled to the diluent bottle through a change-over valve, and is operated in a two-step mode so as to aspirate the reagent and diluent successively and then to discharge them into a common reaction vessel.

16. An apparatus according to claim 14, further comprising refrigerating means for cooling the reagents in the reagent cassette.

17. An apparatus according to claim 16, in which the reagent cassette is so constructed so that the space in which the reagent bottles are installed is substantially closed, said space being coupled to the refrigerating means so as to circulate cooling air through the reagent cassette, and the reagent cassette comprises a small opening through which the aspiration probes may be inserted into a reagent bottle.

18. An apparatus according to claim 16, further comprising a device for heating the diluent to a given temperature.

19. An apparatus according to claim 18, wherein said heating device is arranged around the aspiration probe of the pump.

20. An apparatus according to claim 14, wherein the reagent cassette is divided into first and second portions, reagent bottles containing reagents which have to be cooled are set in the first portion; reagent bottles containing reagents which do not require cooling are set in the second portion; and the apparatus further includes means for refrigerating the first portion of the reagent cassette.

21. An apparatus according to claim 14, wherein a buffer solution is contained in the diluent bottle as the diluent.

22. An apparatus according to claim 14, wherein the apparatus comprises a plurality of reagent delivery pumps, each coupled to respective one of the diluent bottles each of which may contain different diluents.

23. An apparatus according to claim 13, wherein said reagent bottle moving means comprises a frame member and a reciprocal member arranged movably on the frame member in a rectilinear manner, and wherein the reagent cassette is supported in such a manner as to be capable of sliding back and forth on the frame member, and is engaged with the reciprocal member.

24. An apparatus according to claim 13, wherein the reagent delivery pump is so operated that before aspirating reagent, a small amount of air is aspirated to form an air layer in the tip of the dispensing probe.

25. An apparatus according to claim 24, further comprising a device for detecting whether or not a given amount of reagent has been aspirated into the probe.

26. An apparatus according to claim 25, wherein said detecting device comprises a light source having an elongated light exit, and a light-receiving device, having an elongated light entrance, for receiving light passing through the tip of the probe, said light source and light-receiving element being arranged on opposite sides of the probe tip.

27. An apparatus according to claim 25, wherein said detecting device comprises a pair of electrodes having top ends immersed in the tip of the probe, and a circuit for measuring an electrical resistance between the electrodes.

28. An apparatus according to claim 25, wherein said detecting device comprises a pair of plate-like electrodes opposed to each other on opposite sides of the probe tip to form a capacitor, and a circuit for measuring the capacitance of the capacitor thus formed.

29. An apparatus according to claim 13, further comprising a device for detecting the level of reagent in a reagent bottle.

30. An apparatus according to claim 29, wherein said level-detecting device comprises a light source having an elongated exit which extends in the vertical direction, and a light-receiving element having an entrance which extends in the vertical direction, said light source and light-receiving element being arranged opposite to each other with interposed therebetween a reagent bottle made of transparent or translucent material.

31. An apparatus according to claim 29, wherein said level-detecting device comprises a holder secured to the probe and having a pair of arms extending parallel to the probe, a light source provided at a free end of one of the arms, and a light-receiving element provided at a free end of the other arm, and when said probe is inserted into the reagent bottle, the arms move along the side walls of the bottle with the bottle interposed therebetween.

32. An apparatus according to claim 13, further comprising means for cleaning the outer surface of the tip of aspiration probe.

33. An apparatus according to claim 32, wherein said cleaning means comprise a blotter roll arranged between a re-wind roller and a take-up roller, and a driving member for moving the blotter from the re-wind roller to the takeup roller perpendicular to the traveling path of the aspiration probe, the outer surface of which, is cleaned in the process of piercing the blotter.

34. An apparatus according to claim 13, wherein said reagent bottles and reagent cassette comprise indexing means to allow setting of a given reagent bottle into a given position of the reagent cassette.

35. An apparatus according to claim 13, further comprising means for determining the order of reagent aspiration used to carry out predetermined test items for respective samples in such a manner that the traveling distance of the reagent bottles during change-over can be minimized.

36. An apparatus according to claim 35, wherein said order determining means comprise a memory for storing information about the order of arrangement of the reagent bottles in the cassette, a device for producing information denoting a particular bottle which is currently in the delivery position, input means for supplying information about test items pre-determined for respective samples, and calculating means for receiving said order, bottle denoting, and test item information and a device to supply a signal to the reagent bottle moving means.

37. An apparatus according to claim 2, wherein the test liquid discharging means comprise a device for spilling the test liquid out of the reaction vessel, a container for collecting the empty reaction vessels, and a container for gathering the spilt test liquid.

38. An apparatus according to claim 37, further comprising a neutralizing tank for converting the waste test liquid into a relatively harmless liquid before being passed on to a waste liquid container.

39. An apparatus according to claim 2, wherein said reaction vessel is formed as a molded integral body of transparent material including a rectangular opening, a supporting flange provided at the periphery of said opening, tapered side wall narrowing toward the bottom, and a semi-cylindrical bottom portion having upright semi-circular end windows through which photometry is effected.

40. An apparatus according to claim 39, wherein a light source and a light-receiving element of the photometry means are arranged on an optical axis parallel to the longitudinal axis of the semi-cylinder and a light-receiving element for receiving a scattered and/or fluorescent light emitted from the semi-cylindrical portion of the reagent vessel in a direction different than said optical axis.

41. An apparatus according to claim 2, wherein said reaction vessel comprises transparent entrance and exit plan walls parallel to each other, the light source and a light-receiving element of the photometry means are arranged on an optical axis perpendicular to said plane walls, and the reaction vessel is so arranged as to be capable of being inclined with respect to said optical axis so as to carry out transmitted light measurement and/or scattered and/or fluorescent light measurement by means of a common light source and light-receiving element.

42. An apparatus according to claim 2, wherein the reaction vessel has transparent entrance and exit walls parallel to each other and a transparent bottom, a light source of the photometry means is arranged on an optical axis perpendicular to the walls, a light-receiving element of the photometry means is arranged to receive scattered and/or fluorescent light emitted through the bottom and a reflecting mirror is so arranged on said optical axis as to reflect transmitted light onto the light-receiving element, said mirror is further so arranged as to be capable of being turned to such a position that the transmitted light does not enter into the light-receiving element.

43. An apparatus according to claim 2, wherein the light source and a light-receiving element of the photometry means are arranged on an optical axis through which reaction vessels are transported and the reaction vessels have two different configurations. In one of the configurations, the light being able to pass through the reaction vessel along said optical axis, and in the other configuration, scattered and/or fluorescent light being able to impinge upon the light-receiving element along the optical axis.

44. An apparatus according to claim 1, further comprising a device for preferentially measuring the ionic activity of various ionic species present in a test liquid in a measuring cell, and device for transporting a test liquid container in a reaction vessel into said measuring cell.

45. An apparatus according to claim 1, further comprising a device for preferentially measuring the ionic activity of various species of ion present in a test liquid contained in a reaction vessel.

46. An apparatus according to claim 11, wherein in order to automatically calibrate the apparatus, the sample feeding means comprises a position into which a 'standard' sample for calibration may be set, and the apparatus further comprises means for effecting calibration by means of said standard sample at a given time interval during a stand-by condition.

47. An apparatus according to claim 1, further comprising a dedicated control device which includes a computer and an interface, and a switching device through which the computer of the dedicated control device or a computer installed at a remote location can be selectively connected to the apparatus.

48. An apparatus according to claim 1, further comprising a dedicated control device which includes a computer.

49. An apparatus according to claim 1, further comprising means for printing on a report form a measured result for a given test item and an expected value range of this test item corresponding to a given patient population.

50. An apparatus according to claim 49, wherein said printing means further prints a comparison result between the expected range and the measured result on the patient card.

* * * * *